US008828986B2

(12) United States Patent
Hurt et al.

(10) Patent No.: US 8,828,986 B2
(45) Date of Patent: Sep. 9, 2014

(54) ANTIVIRAL COMPOUNDS

(75) Inventors: Clarence Hurt, Los Altos, CA (US);
Andy Atuegbu, Dublin, CA (US);
Anatoliy Kitaygorodskyy, San Francisco, CA (US); Beverly Freeman, Albany, CA (US); Vishwanath Lingappa, San Francisco, CA (US)

(73) Assignee: Prosetta Antiviral Inc., San Francisco, CA (US)

( * ) Notice: Subject to any disclaimer, the term of this patent is extended or adjusted under 35 U.S.C. 154(b) by 0 days.

(21) Appl. No.: 13/451,608

(22) Filed: Apr. 20, 2012

(65) Prior Publication Data

US 2012/0270854 A1 Oct. 25, 2012

Related U.S. Application Data

(63) Continuation-in-part of application No. 13/099,006, filed on May 2, 2011, and a continuation-in-part of application No. 13/316,423, filed on Dec. 9, 2011, and a continuation-in-part of application No. 13/433,378, filed on Mar. 29, 2012.

(60) Provisional application No. 61/477,203, filed on Apr. 20, 2011, provisional application No. 61/479,351, filed on Apr. 26, 2011, provisional application No. 61/514,825, filed on Aug. 3, 2011.

(51) Int. Cl.
*C07D 417/04* (2006.01)
*C07D 417/14* (2006.01)
*A61K 31/5415* (2006.01)
*A61K 31/551* (2006.01)

(52) U.S. Cl.
USPC ............... 514/210.2; 514/225.2; 514/224.8; 544/35; 544/37; 544/38

(58) Field of Classification Search
USPC ........ 544/35, 37, 38; 514/210.2, 225.2, 224.8
See application file for complete search history.

(56) References Cited

U.S. PATENT DOCUMENTS

| | | | |
|---|---|---|---|
| 4,141,668 A | 2/1979 | Engel | |
| 4,561,001 A | 12/1985 | Gunn et al. | |
| 4,604,458 A | 8/1986 | Hung | |
| 4,714,763 A | 12/1987 | Theodoropulos | |
| 5,344,928 A | 9/1994 | Masuya et al. | |
| 5,532,171 A | 7/1996 | Motsenbocker et al. | |
| 6,194,573 B1 | 2/2001 | Burkett | |
| 6,372,904 B2 | 4/2002 | Burkett | |
| 6,723,893 B1 | 4/2004 | Brown et al. | |
| 6,765,088 B1 | 7/2004 | Korth et al. | |
| 7,276,494 B2 | 10/2007 | Brown et al. | |
| 7,282,215 B2 | 10/2007 | Chowdhary | |
| 7,371,744 B2 | 5/2008 | Brown et al. | |
| 7,407,948 B2 | 8/2008 | Griffiths et al. | |
| 7,407,953 B2 | 8/2008 | Brown et al. | |
| 7,732,439 B2 | 6/2010 | Brown et al. | |
| 7,855,197 B2 | 12/2010 | Brown et al. | |
| 7,915,254 B2 | 3/2011 | Brown et al. | |
| 8,188,074 B2 | 5/2012 | Brown et al. | |
| 8,227,459 B2 | 7/2012 | Plattner et al. | |
| 2002/0111501 A1 | 8/2002 | Burkett | |
| 2003/0022243 A1 | 1/2003 | Kondejewski et al. | |
| 2003/0104577 A1 | 6/2003 | Lingappa, Jr. et al. | |
| 2003/0158204 A1 | 8/2003 | Galey et al. | |
| 2003/0162246 A1 | 8/2003 | Endo et al. | |
| 2006/0177813 A1 | 8/2006 | Endo et al. | |
| 2006/0264423 A1 | 11/2006 | Wood et al. | |
| 2007/0015211 A1 | 1/2007 | Lingappa et al. | |
| 2007/0128633 A1 | 6/2007 | Zozulya et al. | |
| 2007/0202537 A1 | 8/2007 | Lingappa et al. | |
| 2009/0023715 A1 | 1/2009 | Brown et al. | |
| 2009/0155761 A1 | 6/2009 | Hansen et al. | |
| 2010/0204215 A1 | 8/2010 | Galey et al. | |
| 2010/0211327 A1 | 8/2010 | Hahner et al. | |
| 2011/0028459 A1 | 2/2011 | Brown et al. | |
| 2011/0306576 A1 | 12/2011 | Wainwright | |
| 2012/0157435 A1 | 6/2012 | Hurt et al. | |
| 2012/0302557 A1 | 11/2012 | Brown et al. | |
| 2012/0328530 A1 | 12/2012 | Wainwright | |

FOREIGN PATENT DOCUMENTS

| | | |
|---|---|---|
| DE | 196 40 758 | 4/1998 |
| EP | 196515 | 10/1986 |
| EP | 0510668 | 10/1992 |
| GB | 2002517 | 2/1979 |
| GB | 2 083 488 | 3/1982 |
| GB | 2083488 A * | 3/1982 |
| GB | 2373787 | 10/2002 |
| KR | 10-2003-0031992 | 4/2003 |
| WO | WO 90/13296 | 11/1990 |
| WO | WO 98/22150 | 5/1998 |
| WO | WO 98/28607 | 7/1998 |

(Continued)

OTHER PUBLICATIONS

U.S. Appl. No. 11/798,776, filed May 16, 2007, Griffiths et al.
Amaral et al. Phenothiazines: potential management of Creutzfeldt-Jacob disease and its variants, Int. Journal of Antimicrobial Agents 18 (2001) 411-0417.
Andreani, F. et al., Ladder oligophenothiazines by direct thionation of N-Arylanilino Derivatives, (1991) J. Heterocyclic Chem., 28, 295-299.
Arhel et al., Host Proteins Involved in HIV Infection: New Therapeutic Targets, Biochimica et Biophysica Acta, vol. 1802: 313-321, 2010.

(Continued)

*Primary Examiner* — Kahsay Habte
(74) *Attorney, Agent, or Firm* — Morgan, Lewis & Bockius LLP

(57) ABSTRACT

Compounds and methods for preventing and treating viral infections are provided. In some embodiments, novel compounds broad-spectrum antiviral activity are provided. In more specific embodiments, the compounds and methods are effective against viruses such as Venezuelan Equine Encephalitis, West Nile Virus, and Hepatitis C.

64 Claims, No Drawings

(56) References Cited

FOREIGN PATENT DOCUMENTS

| WO | WO 99/25388 | 5/1999 |
|---|---|---|
| WO | WO 02/24226 | 3/2002 |
| WO | WO 02/55720 | 7/2002 |
| WO | WO 02/75318 | 10/2002 |
| WO | WO 02/96896 | 12/2002 |
| WO | WO 2004/033628 | 4/2004 |
| WO | WO 2005/019828 | 3/2005 |
| WO | WO 2005/054217 | 6/2005 |
| WO | WO 2006/032847 | 3/2006 |
| WO | WO 2006/032879 | 3/2006 |
| WO | WO 2006/034219 | 3/2006 |
| WO | WO 2007/038201 | 4/2007 |
| WO | WO 2007/086995 | 8/2007 |
| WO | WO 2007/110627 | 10/2007 |
| WO | WO 2007/110629 | 10/2007 |
| WO | WO 2007/110630 | 10/2007 |
| WO | WO 2008/007074 | 1/2008 |
| WO | WO 2008/124550 | 10/2008 |
| WO | WO 2008/124550 A1 | 10/2008 |
| WO | WO 2008/155533 | 12/2008 |
| WO | WO 2009/044127 | 4/2009 |
| WO | WO 2010/067078 | 6/2010 |
| WO | WO 2010/097626 | 9/2010 |
| WO | WO 2011/114137 | 9/2011 |
| WO | WO 2011/137447 A1 | 11/2011 |
| WO | WO 2012/107706 | 8/2012 |

OTHER PUBLICATIONS

Baker-Wagner et al., "Evidence for Host Drug Targets Essential for Dengue Virus Capsid Formation", poster presented at the International Conference on Antiviral Research (ICAR) in San Francisco, CA, Apr. 25-28, 2010.
Bewley, G.C.: cDNA and deduced amino acid sequence of murine Cu—Zn superoxide dismutase, Nucleic Acids Research Mar. 25, 1988, vol. 16 No. 6 Mar. 25, 1988, p. 2728.
Bieniasz, P., Restriction Factors: a Defense Against Retroviral Infection, Trends in Microbiology, vol. 11: 286-291, 2003.
Chang, T.W. et al., Photodynamic inactivation of herpesvirus hominins by methylene blue (38524). (1975) Proc Soc Exp Biol Med vol. 148 pp. 291-293.
Cheng NG C C: Novel common structural feature among several classes of antimalarial agents, Journal of Pharmaceutical Sciences, American Pharmaceutical Association, Washington, US, val. 63, No. 2, Feb. 1, 1974, pp. 307-310, XP009132753, ISSN: 0022-3549.
Cobo, M.F., Photodynamic inactivation of Junin virus, (1986) Med. Microbiol. Immunol., 175, 67-69.
Coetzer et al., Erythrocyte Membrane Proteins in Hereditary Glucose Phosphate Isomerase Deficiency, J. Clinical Investigation 63 (4): 552-561 (1979), abstract only.
Creed et al., Ground and excited state properties of some new highly water soluble N-substituted thiazine dyes for photogalvanic applications, J. Chem. Soc., Chem. Commun., 1983, 1521-1523.
Creighton T.E. Proteins, Structures and Molecular Properties, 2nd E. pp. 31-35., © 1993,1984 by W.H. Freeman and Company.
Dooher et al., Cell-Free Systems for Capsid Assembly of Primate Lentiviruses from Three Different Lineages, The Journal of Medical Primatology, vol. 33: 272-280, 2004.
Feigenbaum, J., Receptor inactivation by dye-neuropeptide conjugates: 1. The synthesis of Cys-containing dye-neuropeptide conjugates., Peptides, vol. 17, No. 6, pp. 991-994, 1996.
Francis et al., "Efficacy of a Small Molecule Inhibitor of Ebola Capsid Assembly in an Animal Model", poster presented at the International Conference on Antiviral Research (ICAR) in San Francisco, CA, Apr. 25-28, 2010.
Haurum J.S., Recombinant polyclonal antibodies: the next generation of antibody therapeutics?, Drug Discovery Today, 11(13/14), Jul. 2006.
Karpuj et al., "Small Molecule Therapeutics of Viruses of Families Bunyaviridae and Arenaviridae", poster presented at the International Conference on Antiviral Research (ICAR) in San Francisco, CA, Apr. 25-28, 2010.

Khattab, M., Targeting Host Factors: a Novel Rationale for the Management of Hepatitis C Virus, World Journal of Gastroenterology, vol. 15: 3472-3479, 2009.
Khutormenko et al, 3,7-Diamino-10-Acetylphenothiazine, UDC 615.31:547.869.2. 012.1, Institute of Pharmacology, Academy of Medical Sciences of the USSR, Moscow. Translated from Khimiko-Farmatsevticheskii Zhurnal, vol. 10, No. i, pp. 92-97, Jan., 1976. Original article submitted Apr. 4, 1975.
Klein et al., HIV Gag-leucine zipper chimeras form ABCE1-containing intermediates and RNase-resistant immature capsids similar to those formed by wild-type HIV-1 Gag, The Journal of Virology, vol. 85:7419-35, 2011.
Klein et al., Identification of Residues in the Hepatitis C Virus Core Protein That Are Critical for Capsid Assembly in a Cell-Free System., Journal of Virology, vol. 79: 6814-6826, 2005.
Klein et al., Unique Features of Hepatitis C Virus Capsid Formation Revealed by De Novo Cell-Free Assembly, Journal of Virology, vol. 78: 9257-9269, 2004.
Komano et al., The Interaction of HIV-1 with the Host Factors., Japanese Journal of Infectious Diseases, vol. 58: 125-130, 2005.
Lambrecht, Rapid inactivation of HIV-1 in single donor preparations of human fresh frozen plasma by methylene blue/light treatment, Biologicals (1994) 22, 227-231.
Lawrason et al., Correlation between the mean corpuscular volume and reticulocytosis in phenlhydrazine anemia in swine, Blood 4 : 1256-1263 (1949).
Lingappa et al., "Overlap in Virus Specificity Leads to the Discovery of Small Molecules Active Against Rabies Virus, Monkey Pox Virus and Cytomegalovirus", poster presented at the International Conference on Antiviral Research (ICAR) in San Francisco, CA, Apr. 25-28, 2010.
Lingappa et al., "Cell-free Protein Synthesizing Systems as Tools for Discovery of Drugs Inhibiting Viral Capsid Assembly", poster presented at the International Conference on Antiviral Research (ICAR) in San Francisco, CA, Apr. 25-28, 2010.
Lingappa et al., "Small Molecule Inhibitors of De Novo Cell-free Capsid Assembly Effective Against Flaviridae and Togaviridae", poster presented at the International Conference on Antiviral Research (ICAR) in San Francisco, CA, Apr. 25-28, 2010.
Lingappa et al., A Eukaryotic Cytosolic Chaperonin Is Associated with a High Molecular Weight Intermediate in the Assembly of Hepatitis B Virus Capsid, a Multimeric Particle., The Journal of Cell Biology, vol. 125: 99-111, 1994.
Lingappa et al., A Multistep, ATP-Dependent Pathway for Assembly of Human Immunodeficiency Virus Capsids in a Cell-Free System, The Journal of Cell Biology, vol. 136: 567-581, 1997.
Lingappa et al., Comparing Capsid Assembly of Primate Lentiviruses and Hepatitis B Virus Using Cell-Free Systems., Virology, vol. 333: 114-123, 2005.
Lingappa et al., Recent Insights into Biological Regulation from Cell-Free Protein-Synthesizing Systems., The Mount Sinai Journal of Medicine, vol. 72: 141-160, 2005.
Lingappa, Jr. et al., A Eukaryotic Cytosolic Chaperonin is Associated with a High Molecular Weight Intermediate in the Assembly of Hepatitis B Virus Capsid, a Multimeric Particle, The Journal of Cell Biology, Apr. 1994, vol. 125. No. 1. pp. 99-111.
Loach, Thin-layer chromatographic separation of methylene blue and related thiazine dyes, J.Chromatography, 60 (1971) 119-126.
Long, Experimental Anemia Produced by Phenylhydrazine Derivatives, J. Clinical Investigation 11(4): 329-339 (1926).
Lunsden et al., The Kinetics of Hematopoiesis in the Light Horse III. The Hematological Response to Hemolytic Anemia, Can. J. Comp. Med. 39 : 32-339 Jul. (1975).
Mascarenhas et al., The Capsid Protein of Human Immunodeficiency Virus: Interactions of HIV-1 Capsid with Host Protein Factors., FEBS Journal, vol. 276: 6118-6127, 2009.
Mellish et al., In vitro photodynamic activity of a series of methylene blue analogues, Photochemistry and Photobiology, 2002, 75(4): 392-397.
Motsenbocker et al Photochemistry and Photobiology. vol. 58, No. 5, pp. 648-652, 1993.

(56) References Cited

OTHER PUBLICATIONS

Motsenbocker, et al., Establishment of the Optically Pumped Chemiluminescence Technique for Diagnostics, Anal. Chem. 1993, 65,403-400.
Moura et al, 3,7-Bis(dialkylamino)phenothiazin-5-ium Derivatives: Biomedical Applications and Biological Activity, Current Drug Targets, 2003, vol. 4, No. 2.
Moura, J.C.V.P., Synthesis and Evaluation of Phenothiazine Singlet Oxygen Sensitizing Dyes for Application in Cancer Phototherapy, (1997) Phosphorus, Sulfur Silicon, vol. 120 & 121, pp. 459-460.
Muller-Breitkreutz et al., Hepatitis C and Human Immunodeficiency Virus RNA Degradation by Methylene Blue/Light Treatment of Human Plasma, Journal of Medical Virology 56:239-245 (1998).
Palacios et al., Panmicrobial oligonucleotide array for diagnosis of infectious diseases, Emerging Infectious Diseases, vol. 13 No. 1, p. 73-81, Jan. 2007.
Papin et al., Methylene blue photoinactivation abolishes West Nile virus infectivity in vivo, Antiviral Research, Elsevier Science BV., Amsterdam, NL, vol. 68, No. 2, Nov. 1, 2005, pp. 84-87.
Pardo C A et al., Superoxide dismutase is an abundant component in cell bodies, dendrites, and axons of motor neurons and in a subset of other neurons, Proceedings of the National Academy of Sciences of the United States of America Feb. 14, 1995, vol. 92, No. 4, Feb. 14, 1995, pp. 954-958.
Petsch et al., "Discovery of Novel Small Molecule Inhibitors of Multiple Influenza-A Strains in Vivo", poster presented at the International Conference on Antiviral Research (ICAR) in San Francisco, CA, Apr. 25-28, 2010.
Rakhit Rishi et al., An immunological epitope selective for pathological monomer-misfolded SOD1 in ALS, Nature Medicine Jun. 2007, vol. 13, No. 6, Jun. 2007 pp. 754-759.
Rakhit Rishi et al., Monomeric Cu, Zn-superoxide dismutase is a common misfolding intermediate in the oxidation models of sporadic and familial amyotrophic lateral sclerosis, The Journal of Biological Chemistry Apr. 9, 2004, vol. 279, No. 15, Apr. 9, 2004, pp. 15499-15504.
Ray Soumya S. et al. Small-molecule-mediated stabilization of familial amyotrophic lateral sclerosis-linked superoxide dismutase mutants against unfolding and aggregation, Proceedings of The National Academy of Sciences of the United States of America Mar. 8, 2005, vol. 102, No. 10, Mar. 8, 2005 pp. 3639-3644.
Reed et al., HIV-1 Gag co-opts a cellular complex containing DDX6, a helicase that facilitates capsid assembly, The Journal of Cell Biology, vol. 198(3):439-56, 2012.
Robuschi, L. Sperimentale (1940) 94, 99-124.
Rosenberg et al., Messenger RNA Loses the Ability to Direct in Vitro Peptide Synthesis following incubation with Cisplatin, Molecular Pharmacology 33 (6): 611-616 (1988).
Shapira et al., A Physical and Regulatory Map of Host-Influenza Interactions Reveals Pathways in H1N1 Infection, Cell, vol. 139: 1255-1267, 2009.
Sherman L. et al., Nucleotide Sequence and Expression of Human Chromosome 21-encoded superoxide Dismutase MRNA, Proceedings of the National Academy of Science, Washington, DC, US, vol. 80, Sep. 1983, pp. 5465-5469.
Singh et al., Effect of Mutations in Gag on Assembly of Immature Human Immunodeficiency Virus Type 1 Capsids in a Cell-Free System, Virology, vol. 279: 257-270, 2001.
Stertz et al., Human host factors required for influenza virus replication, Nature. Feb. 11, 2010;463(7282):813-7.
Stremlau, S., Why Old World Monkeys Are Resistant to HIV-1, Science, vol. 318: 1565-1566, 2007.
Swartz, M.R. et al., Inactivation of herpes simplex virus with methylene blue, light, and electricity, (1979) Proc Soc Exp Biol Med 161(2) 204-209.
Tai M M et al., Conformation specific antibodies directed against the Bovine Prothrombin Calcium Complex, Journal of Biological Chemistry, vol. 255, No. 7, 1980, pp. 2790-2795.
Valenty, Monolayer films of surfactant derivatives of methylene blue, Journal of Colloid and Interface Science, vol. 68, No. 3, Mar. 1, 1979.
Visalli et al., DNA Encapsidation as a Target for Anti-Herpesvirus Drug Therapy, Antiviral Research, vol. 59: 73-87, 2003.
Voet et al. Biochemistry, 2nd. Ed. pp. 107-112., © 1995 by John Wiley & Sons, Inc.
Wagner et al., Factors affecting virus photoinactivation by a series of phenothiazine dyes, Photochem Photobiol. Mar. 1998;67(3):343-9.
Wainwright et al., Methylene blue derivatives—suitable photoantimicrobials for blood product disinfection, International Journal of Antimicrobial Agents 16 (2000) 381-394.
Wainwright Mark, Richard M. Giddens, Phenothiazinium photosensitisers: choices in synthesis and application, Dyes and Pigments 57 (2003) 245-257.
Wang et al. Microarray-based detection and genotyping of viral pathogens, PNAS, vol. 99, No. 24, p. 15687-15692, Nov. 26, 2002.
Zimmerman et al., Identification of a Host Protein Essential for Assembly of Immature HIV-1 Capsids, Nature, vol. 415: 88-92, 2002.
Lucjan Strekowski, et al., "A Synthetic Route to 3-(Dialkylamino) phenothiazin-5-ium Salts and 3,7-Disubstituted Derivatives Containing Two Different Amino Groups", Department of Chemistry, J. Heterocyclic Chem. 30, pp. 1693-1695 (1993).

\* cited by examiner

ANTIVIRAL COMPOUNDS

1 CROSS-REFERENCE TO RELATED APPLICATIONS

This application is a continuation-in-part of U.S. patent application Ser. No. 13/099,006 filed 2 May 2011 and is a continuation-in-part of Ser. No. 13/316,423 filed 9 Dec. 2011 and is a continuation-in-part of Ser. No. 13/433,378 filed 29 Mar. 2012, and claims priority to provisional U.S. Patent Application Ser. No. 61/477,203 filed 20 Apr. 2011, 61/479,351 filed 26 Apr. 2011, and 61/514,825 filed 3 Aug. 2011, the entire disclosure of U.S. Patent Application Ser. No. 61/477,203 filed 20 Apr. 2011 is incorporated herein by reference in its entirety and for all purposes.

2 BACKGROUND OF THE INVENTION

1. Field of the Invention

The present invention provides compositions and methods for preventing and treating viral infections. The present invention thus has applications in the areas of medicine, pharmacology, virology, and medicinal chemistry.

2. The Related Art

Few good options are available for preventing or treating viral infections. The vast majority of antiviral drugs interfere with viral replication through the inhibition of transcription of the viral genome. Commonly these drugs inhibit a specific protein involved in viral genomic transcription, such as a polymerase or transcriptase; which often produces unwanted toxicity, since viruses depend largely on host factors for viral genomic replication. Moreover, given the highly specific nature of the target, small mutations in the viral genome are often sufficient to create viral strains that are resistant to chemotherapeutics. In addition, since the drugs inhibit active viral replication, they cannot eliminate virus that is latent or sequestered in the host; thus, patients are forced to take antivirals and endure their toxic effects for long periods if not indefinitely. Not surprisingly, patients on such regimens cannot continue treatment, and remain infected as well as providing a potentially continuing source of additional infections.

Thus there is a need for better antiviral chemotherapeutics and more effective strategies for identifying such chemotherapeutics. The need is especially urgent for those suffering from chronic and debilitating viral infections, such as human immunodeficiency virus (HIV) and hepatitis C(HCV), for which no good treatment exists for the reasons noted above.

But new viral threats are also on the horizon. The steady encroachment of civilization into the most remote regions of the globe has introduced the risk of exotic viral infections to the population at large. Each passing year brings an increasing number of reports of infections by hemorragic fevers, such as Ebola virus (EBOV), Marburg virus (Marburg), and Rift Valley Fever virus (RVFV). Still other viral infections can cause potentially debilitating effects, such as recurrent fevers, joint pain, and fatigue; these include: Punta Toro Virus (PTV), West Nile virus (WNV), chikungunya virus (CHK), Easter Equine Encephalitis virus (EEEV), Western Equine Encephalitis virus (WEEV), Lhasa virus (LASV), and Dengue virus (DENV).

By way of example, one of the additional "new" viruses (that is, new with respect to the industrialized world) is Venezuelan Equine Encephalitis virus (also called Venezuelan equine encephalomyelitis, VEEV). VEEV is a mosquito-borne viral disease of all equine species, including horses, asses (wild and domestic), and zebras. Equines infected with VEEV may show one or more of the following signs: fever, depression, loss of appetite weakness, and central nervous system disorders (lack of coordination, chewing movements, head pressing, "sawhorse" stance, circling, paddling motion of the limbs, and convulsions). In some cases, horses infected with VEEV may show no clinical signs before dying. The clinical signs of VEEV can be confused with those of other diseases that affect the central nervous system. These include eastern equine encephalitis, western equine encephalitis, African horse sickness, rabies, tetanus, and bacterial meningitis. VEE might also be mistaken for toxic poisoning. Definitive diagnosis can be made by isolating the virus in a laboratory or by testing blood for the presence of antibodies to the virus.

Humans also can contract this disease. Healthy adults who become infected by the virus may experience flu-like symptoms, such as high fevers and aches; and those having weakened immune systems, as well as the young and elderly, can become more severely ill or even die.

The virus that causes VEEV is transmitted primarily by mosquitoes that bite an infected animal and then bite and feed on another animal or human. The speed with which the disease spreads depends on the subtype of the VEEV virus and the density of mosquito populations. Enzootic subtypes of VEEV are diseases endemic to certain areas. Generally these serotypes do not spread to other localities. Enzootic subtypes are associated with the rodent-mosquito transmission cycle. These forms of the virus can cause human illness but generally do not affect equine health. Epizootic subtypes, on the other hand, can spread rapidly through large populations. These forms of the virus are highly pathogenic to equines and can also affect human health. Equines, rather than rodents, are the primary animal species that carry and spread the disease. Infected equines develop an enormous quantity of virus in their circulatory system. When a blood-feeding insect feeds on such animals, it picks up this virus and transmits it to other animals or humans. Although other animals, such as cattle, swine, and dogs, can become infected, they generally do not show signs of the disease or contribute to its spread.

Naturally occurring outbreaks of VEEV are rare. In 1936, VEEV was first recognized as a disease of concern in Venezuela following a major outbreak of equine encephalomyelitis. From 1936 to 1968, equines in several South American countries suffered devastating outbreaks. In 1969, the disease moved north throughout Central America, finally reaching Mexico and Texas in 1971. The highly pathogenic form of VEEV has not occurred in the United States since 1971. However, in 1993 an outbreak of VEEV in the State of Chiapas, Mexico, prompted the U.S. Department of Agriculture to temporarily increase its surveillance activities and tighten its quarantine requirements for equine species entering the United States from Mexico. During outbreaks, the most effective way to prevent further spread of disease is to quarantine infected equines. Controlling mosquito populations through pesticide treatments and eliminating insect-breeding sites will also enhance disease control. These measures should be accompanied by a large-scale equine immunization program. Equines in the United States should be vaccinated for VEE only when there is a serious threat that the disease could spread to this country.

Similar to VEE is West Nile virus (WNV), which was mentioned above. West Nile virus is named for a district in Uganda where the virus was first identified in humans in 1937. Outbreaks of the virus have occurred in a number of countries throughout Europe, the Middle East, Africa, Central Asia, and Australia, since that time. WNV was first detected in the Western Hemisphere in 1999, and since then the disease has spread across North America, Mexico, Puerto Rico, the Dominican Republic, Jamaica, Guadeloupe, and El Salvador. Symptoms range from a mild, flu-like illness (fever, headache, muscle and joint pain) and a red, bumpy rash, to meningitis. In rare cases those infected will develop encephalitis, which can include high fever, a stiff neck, disorientation, paralysis, convulsions, coma, and death in about ten percent of cases.

No cure or treatment is available for either VEEV or WNV, or the other viruses listed above; so public health experts emphasize prevention by avoiding areas where the disease has been detected or where disease vectors (usually mosquitoes) have been identified. However, that approach is becoming less reasonable as the world population grows. Moreover, some officials fear that one or both of these diseases, or other similar viruses in the toga- and flaviviridae, could be "weaponized" by a hostile government or terrorist organization to immobilize military personnel or important segments of the population in an attack.

To make matters still more complicated, the above-mentioned viral threats span almost all of the recognized viral families, including the bunyaviruses, flaviviruses, filoviruses, arenaviruses, and togaviruses. Since viral families are defined in significant part by their differences in mechanism for genomic replication, therapeutic strategies that are focused on inhibiting genomic replication will be inadequate for large outbreaks of new, and especially weaponized, viruses.

PCT Publication WO 2008/124550 discloses small molecule therapeutics having "broad spectrum" antiviral properties. Nevertheless, there remains an acute need to provide medicinal treatments for viral diseases. The present invention meets these and other needs.

3 SUMMARY OF EMBODIMENTS OF THE INVENTION

The present invention provides a variety of compounds, methods, and compostions for treating viral infections, especially those described above. In particular, as will become readily apparent to those having ordinary skill in the art upon reading the following, the present invention provides compounds, methods, and compositions for "broad-spectrum" anti-viral treatments by providing compounds that are effective against multiple viruses, often from multiple viral families.

In a first aspect, the present invention provides novel compounds having the structure:

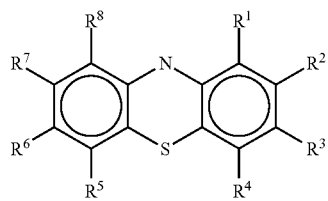

and their pharmaceutically acceptable salts, hydrates, and coordination compounds. $R^1$, $R^2$, $R^4$, $R^5$, $R^7$, and $R^8$ are selected independently from the group consisting of: hydrogen, halo, cyano, nitro, thio, amino, carboxyl, formyl, and alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkycarbonylthiooxy, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted. $R^3$ and $R^6$ are selected independently from the group consisting of: amino, optionally substituted alkylamino, optionally substituted dialkylamino, and optionally substituted four-, five-, six-, seven-, and eight-membered cycloheteroalkyl, said optionally substituted four-, five-, six-, seven-, and eight-membered cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, optionally substituted sulfinyl, and optionally substituted sulfonyl; and dialkylimino, diarylimino, di-heteroarylimino, alkylarylimino, alkylheteroarylimino, arylheteroarylimino, amino, alkylamino, dialkylamino, alkyloxyalkylamino, di-(alkyloxyalkyl)amino, alkylthioalkylamino, di-(alkylthioalkyl)amino, alkylaminoalkylamino, di-(alkylaminoalkyl)amino, aryloxyalkylamino, di(aryloxyalkyl)amino, arylthioalkylamino, di-(arylthioalkyl)amino, arylaminoalkylamino, di-(arylaminoalkyl)amino, heteroaryloxyalkylamino, di-(heteroaryloxyalkyl)amino, heteroarylthioalkylamino, di-(heteroarylthioalkyl)amino, heteroarylaminoalkylamino, and di-(heteroarylaminoalkyl)amino, each of which is optionally substituted. At least one of $R^3$ and $R^6$ is optionally substituted morpholin-1-yl.

In more specific embodiments, $R^3$ is optionally substituted morpholin-1-yl. In still more specific embodiments, in addition to the foregoing each of $R^2$, $R^4$, $R^5$, and $R^7$ is hydrogen. Yet more specific embodiments include those for which $R^1$ and $R^8$ are selected independently from the group consisting of hydrogen and optionally substituted alkyl in addition to those details just recited. Still more specific are those embodiments in which $R^1$ and $R^8$ are selected independently from the group consisting of hydrogen, optionally substituted methyl, and optionally substituted ethyl.

Among the latter compounds described above, still further more specific embodiments include those wherein $R^6$ is selected from the group consisting of: amino and optionally substituted alkylamino, optionally substituted dialkylamino, optionally substituted alkyloxyalkylamino, and optionally substituted di-(alkyloxyalkyl)amino; of still more specificity among those embodiments just recited are those in which $R^6$ is optionally substituted dialkylamino, and yet more particularly, those compounds wherein $R^6$ is optionally substituted di-(alkyloxyalkyl)amino.

Other embodiments of the invention include compounds having the structure:

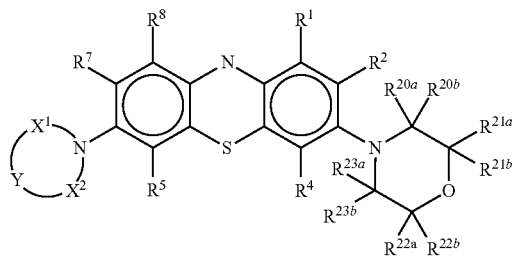

and their pharmaceutically acceptable salts, hydrates, and coordination compounds. Y is $CR^9R^{10}$, $NR^{11}$, O, S, SO, $SO_2$, $SOR^{12}$, and $SO_2R^{13}$, a single bond, or double bond; and $X^1$ and $X^2$ are and $(CR^{16}R^{17})_n$ respectively, wherein each of m and n is either 1, 2, or 3 such that the sum m+n is either 2, 3, 4, 5, or 6, and for each of the m and n methylene units of $X^1$ and $X^2$, each of $R^{14}$-$R^{17}$ is selected independently from the group consisting of: hydrogen, halo, cyano, nitro, thio, amino, carboxyl, formyl, alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl) alkylcarbonyloxy, alkylcarbonyl, arylcarbonyl, heteroarylcarbonyl, cycloalkylcarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkycarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted. Each of $R^{20a}$-$R^{23b}$ is selected independently from the group consisting of: hydrogen, halo, cyano, nitro, thio, amino, carboxyl, formyl, alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkycarbonylthiooxy, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

Among the compounds just described, more specific embodiments include those in which m=n=2. Still more specific embodiments further include those for which $R^1$ and $R^8$ are selected independently from the group consisting of hydrogen and optionally substituted alkyl, and, still more specifically, those in which $R^1$ and $R^8$ are selected independently from the group consisting of hydrogen, optionally substituted methyl, and optionally substituted ethyl.

Still more specific embodiments are those for which m=n=2. Still more specific embodiments further include those in which $R^1$ and $R^8$ are selected independently from the group consisting of hydrogen, optionally substituted methyl, and optionally substituted ethyl and Y is O.

Still more specific embodiments are those for which m=n=2. Still more specific embodiments further include those in which $R^1$ and $R^8$ are selected independently from the group consisting of hydrogen, optionally substituted methyl, and optionally substituted ethyl and Y is $NR^{11}$.

Still more specific embodiments are those for which m=n=2. Still more specific embodiments further include those in which $R^1$ and $R^8$ are selected independently from the group consisting of hydrogen, optionally substituted methyl, and optionally substituted ethyl and Y is a single bond.

Yet other more specific embodiments include those for which m=3 and n=2. Among these embodiments are compounds in which Y is $NR^{11}$. Still more detailed embodiments further include compounds in which $R^1$ and $R^8$ are selected independently from the group consisting of hydrogen and optionally substituted alkyl, and even more particularly, those in which $R^1$ and $R^8$ are selected independently from the group consisting of hydrogen, optionally substituted methyl, and optionally substituted ethyl.

In another aspect, the invention provides a method for treating a viral disease in a mammal afflicted with such disease, comprising administering to such mammal a therapeutically effective amount of a compound of described herein.

4 DETAILED DESCRIPTION OF SOME EMBODIMENTS OF THE INVENTION

4.1 Definitions

The following terms are used herein as defined below unless specifically stated otherwise:

Optionally substituted refers to the replacement of hydrogen with a univalent or divalent radical. Suitable substitution groups include, for example, hydrooxyl, nitro, amino, imino, cyano, halo, thio, thioamido, amidino, oxo, oxamidino, methoxamidino, imidino, guanidino, sulfonamido, carboxyl, formyl, lower alkyl, haloloweralkyl, loweralkoxy, haloloweralkoxy, lower alkoxyalkyl, alkylcarbonyl, arylcarbonyl, aralkylcarbonyl, het eroarylcarbonyl, het eroaralkylcarbonyl, alkylthio, aminoalkyl, cyanoalkyl, and the like as defined herein. The substitution group can itself be substituted. The group substituted onto the substitution group can be, for example, carboxyl, halo; nitro, amino, cyano, hydroxyl, loweralkyl, loweralkoxy, aminocarbonyl, —SR, thioamido, —$SO_3H$, —$SO_2R$ or cycloalkyl, where R is typically hydrogen, hydroxyl or loweralkyl. When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

Loweralkyl as used herein refers to branched or straight chain alkyl groups comprising one to ten carbon atoms that independently are unsubstituted or substituted, e.g., with one or more halogen, hydroxyl or other groups. Examples of loweralkyl groups include, but are not limited to, methyl, ethyl, propyl, isopropyl, n-butyl, t-butyl, n-hexyl, neopentyl, trifluoromethyl, pentafluoroethyl, and the like.

Alkylenyl refers to a divalent straight chain or branched chain saturated aliphatic radical having from 1- to 20 carbon atoms. Typical alkylenyl groups employed in compounds of the present invention are loweralkylenyl groups that have from 1 to about 6 carbon atoms in their backbone.

Alkenyl refers herein to straight chain, branched, or cyclic radicals having one or more double bonds and from 2 to 20 carbon atoms.

Alkynyl refers herein to straight chain, branched, or cyclic radicals having one or more triple bonds and from 2 to 20 carbon atoms.

Haloloweralkyl refers to a loweralkyl radical substituted with one or more halogen atoms.

Loweralkoxy as used herein refers to RO— wherein R is loweralkyl. Representative examples of loweralkoxy groups include methoxy, ethoxy, t-butoxy, trifluoromethoxy and the like.

Loweralkylthio as used herein refers to RS— wherein R is loweralkyl.

Alkoxyalkyl refers to the group -alk$_1$-O-alk$_2$, where alk$_1$ is alkylenyl or alkenyl, and alk$_2$ is alkyl or alkenyl.

Loweralkoxyalkyl refers to an alkoxyalkyl as defined above, where alk$_1$ is loweralkylenyl or loweralkenyl, and alk$_2$ is loweralkyl or loweralkenyl.

Aryloxyalkyl refers to the group alkylenyl-O-aryl. The term Aralkoxyalkyl refers to the group alkylenyl-O-aralkyl, where aralkyl is a loweraralkyl.

Cycloalkyl refers to a mono- or polycyclic, loweralkyl substituent. Typical cycloalkyl substituents have from 3 to 8 backbone (i.e., ring) atoms in which each backbone atom is optionally substituted carbon. When used in context with cycloalkyl substituents, the term polycyclic refers herein to fused, non-fused cyclic carbon structures and spirocycles. Examples of cycloalkyl groups include, but are not limited to, cyclopropyl, cyclobutyl, cyclopentyl, cyclohexyl, adamantyl, bornyl, norbornyl, and the like.

Cycloheteroalkyl refers herein to cycloalkyl substituents that have from 1 to 5, and more typically from 1 to 4 heteroatoms (i.e., non-carbon atoms such as nitrogen, sulfur, and oxygen) in the ring structure, with the balance of atoms in the ring being optionally substituted carbon. Representative heterocycloalkyl moieties include, for example, morpholino, piperazinyl, piperidinyl, pyrrolidinyl, methylpryolidinyl, pyrrolidinone-yl, and the like.

(Cycloalkyl)alkyl and (Cycloheteroalkyl)alkyl refer to alkyl chains substituted with cycloalkyl and cycloheteroalkyl groups respectively.

Haloalkoxy refers to an alkoxy radical substituted with one or more halogen atoms. The term haloloweralkoxy refers to a loweralkoxy radical substituted with one or more halogen atoms.

Halo refers herein to a halogen radical, such as fluorine, chlorine, bromine, or iodine.

Aryl refers to monocyclic and polycyclic aromatic groups, or fused ring systems having at least one aromatic ring, having from 3 to 14 backbone carbon atoms. Examples of aryl groups include without limitation phenyl, naphthyl, dihydronaphtyl, tetrahydronaphthyl, and the like.

Aralkyl refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Heteroaryl refers herein to aryl groups having from one to four heteroatoms as ring atoms in an aromatic ring with the remainder of the ring atoms being aromatic or non-aromatic carbon atoms. When used in connection with aryl substituents, the term polycyclic refers herein to fused and non-fused cyclic structures in which at least one cyclic structure is aromatic, such as, for example, benzodioxozolo, naphthyl, and the like. Exemplary heteroaryl moieties employed as substituents in compounds of the present invention include pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

Amino refers herein to the group —NH$_2$. The term loweralkylamino refers herein to the group —NRR' where R and R' are each independently selected from hydrogen or loweralkyl. The term arylamino refers herein to the group —NRR' where R is aryl and R' is hydrogen, loweralkyl, aryl, or aralkyl. The term aralkylamino refers herein to the group —NRR' where R is aralkyl and R' is hydrogen, loweralkyl, aryl, or aralkyl. The terms heteroarylamino and heteroaralkylamino are defined by analogy to arylamino and aralkylamino.

Aminocarbonyl refers herein to the group —C(O)—NH$_2$. The terms loweralkylaminocarbonyl, arylaminocarbonyl, aralkylaminocarbonyl, heteroarylaminocarbonyl, and heteroaralkylaminocarbonyl refer to —C(O)NRR' where R and R' independently are hydrogen and optionally substituted loweralkyl, aryl, aralkyl, heteroaryl, and heteroaralkyl respectively by analogy to the corresponding terms above.

Thio refers to —SH. The terms loweralkylthio, arylthio, heteroarylthio, cycloalkylthio, cycloheteroalkylthio, aralkylthio, heteroaralkylthio, (cycloalkyl)alkylthio, and (cycloheteroalkyl)alkylthio refer to —SR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Sulfonyl refers herein to the group —SO$_2$—. The terms loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, and (cycloheteroalkyl-) alkylsulfonyl refer to —SO$_2$R where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Sulfinyl refers herein to the group —SO—. The terms loweralkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsulfinyl, and (cycloheteroalkyl)alkylsulfinyl refer to —SOR where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Formyl refers to —C(O)H.

Carboxyl refers to —C(O)OH.

Carbonyl refers to the divalent group —C(O)—. The terms loweralkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, and (cycloheteroalkyl)alkylcarbonyl refer to —C(O)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Thiocarbonyl refers to the group —C(S)—. The terms loweralkylthiocarbonyl, arylthiocarbonyl, heteroarylthio carbonyl, cycloalkylthio carbonyl, cycloheteroalkylthio carbonyl, aralkylthio carbonyloxlthio carbonyl, heteroaralkylthio carbonyl, (cycloalkyl)alkylthio carbonyl, and (cycloheteroalkyl)alkylthio carbonyl refer to —C(S)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Carbonyloxy refers generally to the group —C(O)—O—. The terms loweralkylcarbonyloxy, arylcarbonyloxy, heteroarylcarbonyloxy, cycloalkylcarbonyloxy, cycloheteroallylcarbonyloxy, arallylcarbonyloxy, heteroarallylcarbonyloxy, (cycloallyl)allylcarbonyloxy, (cycloheteroalkyl)allylcarbonyloxy refer to —C(O)OR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Oxycarbonyl refers to the group —O—C(O)—. The terms loweralkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, (cycloheteroalkyl)alkyloxycarbonyl refer to —O—C(O)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Carbonylamino refers to the group —NH—C(O)—. The terms loweralkylcarbonylamino, arylcarbonylamino, hetero arylcarbonylamino, cycloalkylcarbonylamino, cycloheteroalkylcarbonylamino, aralkylcarbonylamino, heteroaralkylcarbonylamino, (cycloalkyl)alkylcarbonylamino, and (cycloheteroalkyl)alkylcarbonylamino refer to —NH—C(O)R, where R is optionally substituted loweralkyl, aryl, heteroaryl, cycloalkyl, cycloheteroalkyl, aralkyl, heteroaralkyl, (cycloalkyl)alkyl, or (cycloheteroalkyl)alkyl respectively. In addition, the present invention includes n-substituted carbonylamino (—NR'C(O)R), where R' is optionally substituted loweralkyl, aryl, heteroaryl, aralkyl, or heteroaralkyl and R retains the previous definition.

Carbonylthio refers to the group —C(O)—S—. The terms loweralkylcarbonylthio, arylcarbonylthio, heteroarylcarbonylthio, cycloalkylcarbonylthio, cycloheteroalkylcarbonylthio, aralkylcarbonylthio, heteroaralkylcarbonylthio, (cycloalkyl)alkylcarbonylthio, (cycloheteroalkyl)alkylcarbonylthio refer to —C(O)SR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Guanidino or Guanidyl refers to moieties derived from guanidine, $H_2N$—C(=NH)—$NH_2$. Such moieties include those bonded at the nitrogen atom carrying the formal double bond (the 2-position of the guanidine, e.g., diaminomethyleneamino, $((H_2N)_2$—C=NH—) and those bonded at either of the nitrogen atoms carrying a formal single bond (the 1- or 3-positions of the guanidine, e.g., $H_2N$—C(=NH)—NH—). The hydrogen atoms at either nitrogen can be replaced with a suitable substituent, such as loweralkyl, aryl, or loweraralkyl.

Amidino refers to the moieties R—C(=N)—NR'— (the radical being at the $N^1$ nitrogen) and R(NR')C=N— (the radical being at the $N^2$ nitrogen), where R and R' can be hydrogen, loweralkyl, aryl, or loweraralkyl.

Imino refers to the group —C(=NR)—, where R can be hydrogen or optionally substituted loweralkyl, aryl, heteroaryl, or heteroaralkyl respectively. The terms iminoloweralkyl, iminocycloalkyl, iminocycloheteroalkyl, iminoaralkyl, iminoheteroaralkyl, (cycloalkyl)minoalkyl, (cycloiminoalkyl)alkyl, (cyclo iminoheteroalkyl)alkyl, and (cycloheteroalkyl)aminoalkyl refer to optionally substituted loweralkyl, cycloalkyl, cycloheteroalkyl, aralkyl, heteroaralkyl, (cycloalkyl)alkyl, and (cycloheteroalkyl)alkyl groups that include an imino group, respectively.

Oximino refers to the group —C(=NOR)—, where R can be hydrogen (hydroximino) or optionally substituted loweralkyl, aryl, heteroaryl, or heteroaralkyl respectively. The terms oximinoloweralkyl, oximinocycloalkyl, oximinocycloheteroalkyl, oximino aralkyl, oximinoheteroaralkyl, (cycloalkyl)oximinoalkyl, (cyclooximino alkyl)alkyl, (cyclo oximinoheteroalkyl)alkyl, and (cycloheteroalkyl)oximinoalkyl refer to optionally substituted loweralkyl, cycloalkyl, cycloheteroalkyl, aralkyl, heteroaralkyl, (cycloalkyl)alkyl, and (cycloheteroalkyl)alkyl groups that include an oximino group, respectively.

Methylene as used herein refers to an unsubstituted, monosubstituted, or disubstituted carbon atom having a formal $sp^3$ hybridization (i.e., —CRR'—, where R and R' are hydrogen or independent substituents).

Methine as used herein refers to an unsubstituted or substituted carbon atom having a formal $sp^2$ hybridization (i.e., CR— or =CR—, where R is hydrogen or a substituent).

4.2 Compounds and Methods of the Invention

In a first aspect, the present invention provides novel compounds having the having the structure (1):

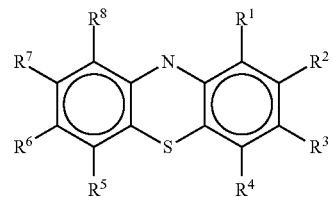

and its pharmaceutically acceptable salts, hydrates, and coordination compounds. $R^1$, $R^2$, $R^4$, $R^5$, $R^7$, and $R^8$ are selected independently from the group consisting of: hydrogen, halo, cyano, nitro, thio, amino, carboxyl, formyl, and alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkycarbonylthiooxy, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted. $R^3$ and $R^6$ are selected independently from the group consisting of: amino, optionally substituted alkylamino, optionally substituted dialkylamino, and optionally substituted four-, five-, six-, seven-, eight-membered cycloheteroalkyl, said optionally substituted four-, five-, six-, seven-, and eight-membered cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, optionally substituted sulfinyl, and optionally substituted sulfonyl; and imino, dialkylimino, diarylimino, di-heteroarylimino, alkylarylimino, alkylheteroarylimino, arylheteroarylimino, amino, alkylamino, dialkylamino, alkyloxyalkylamino, di-(alkyloxyalkyl)amino, alkylthioalkylamino, di-(alkylthioalkyl)amino, alkylamino alkylamino, di-(alkylaminoalkyl)amino, aryloxyalkylamino, di-(aryloxyalkyl)amino, arylthioalkylamino, di-(arylthioalkyl)amino, arylaminoalkylamino, di(arylaminoalkyl)amino, heteroaryloxyalkylamino, di-(heteroaryloxyalkyl)amino, heteroarylthioalkylamino, di-(heteroarylthioalkyl)amino, heteroarylaminoalkylamino, and di-(heteroarylaminoalkyl) amino, each of which optionally substituted. At least one of $R^3$ and $R^6$ is optionally substituted morpholin-1-yl.

In more specific embodiments, $R^3$ of Compound 1 is optionally substituted morpholin-1-yl. In still more specific embodiments, $R^3$ of Compound 1 is optionally substituted morpholin-1-yl and each of $R^2$, $R^4$, $R^5$, and $R^7$ is hydrogen. In yet more specific embodiments, $R^3$ of Compound 1 is optionally substituted morpholin-1-yl, each of $R^2$, $R^4$, $R^5$, and $R^7$ is hydrogen, and $R^4$ and $R^8$ are selected independently from the group consisting of hydrogen and optionally substituted alkyl. Among the latter embodiments are those still more specific embodiments in which $R^4$ and $R^8$ are selected independently from the group consisting of hydrogen, optionally substituted methyl, and optionally substituted ethyl.

In yet more specific embodiments, $R^3$ of Compound 1 is optionally substituted morpholin-1-yl, each of $R^2$, $R^4$, $R^5$, and $R^7$ is hydrogen, $R^4$ and $R^8$ are selected independently from the group consisting of hydrogen, optionally substituted methyl, and optionally substituted ethyl, and $R^6$ is selected from the group consisting of: amino and optionally substituted alkylamino, optionally substituted dialkylamino, optionally substituted alkyloxyalkylamino, and optionally substituted di-(alkyloxyalkyl)amino. Specific examples of these embodiments include, but are not limited to: 3-(dimethylamino)-1,9-dimethyl-7-morpholinophenothiazin-5-ium-4-carboxylic acid; 4-[7-(dimethylamino)-1,9-dimethyl-phenothiazin-5-ium-3-yl]morpholine-2-carboxylic acid; 1-(9-ethyl-1-methyl-7-morpholino-phenothiazin-5-ium-3-yl)-N,N-dimethyl-piperidin-4-amine; ethyl 4-[7-(dimethylamino)-1,9-dimethyl-phenothiazin-5-ium-3-yl]morpholine-2-carboxylate; 3-(bis(2-methoxyethyl)amino)-1,9-dimethyl-7-morpholinophenothiazin-5-ium; 3-(dimethylamino)-7-(2,6-dimethylmorpholino)-1,9-diethylphenothiazin-5-ium iodide; 3-(dimethylamino)-1-ethyl-9-methyl-7-morpholinophenothiazin-5-ium iodide; 3-(2-carboxymorpholino)-7-(dimethylamino)-1,9-dimethylphenothiazin-5-ium iodide; 3-(dimethylamino)-7-(2,6-dimethylmorpholino)-1-ethyl-9-methylphenothiazin-5-ium iodide; and 3-(dimethylamino)-7-(3,5-dimethylmorpholino)-1-ethyl-9-methylphenothiazin-5-ium iodide.

In some embodiments, $R^3$ of Compound 1 is optionally substituted morpholin-1-yl, each of $R^2$, $R^4$, and $R^7$ is hydrogen, $R^5$ is carboxyl, alkyloxycarbonyl, formyl, or cyano, and $R^4$ and $R^8$ are selected independently from the group consisting of hydrogen, optionally substituted methyl, and optionally substituted ethyl, and $R^6$ is selected from the group consisting of: amino and optionally substituted alkylamino, optionally substituted dialkylamino, optionally substituted alkyloxyalkylamino, and optionally substituted di-(alkyloxyalkyl)amino. One non-limiting example is: 4-carboxy-3-(dimethylamino)-1,9-dimethyl-7-morpholinophenothiazin-5-ium iodide.

In some embodiments, $R^3$ is optionally substituted four-, five-, six-, seven-, or eight-membered cycloheteroalkyl having the structure (2):

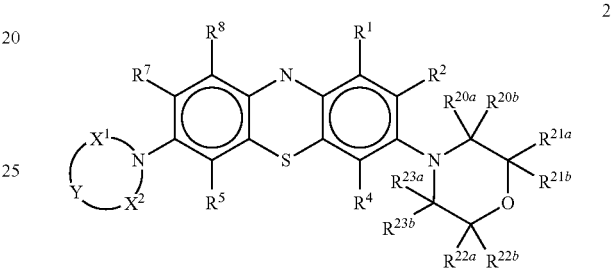

wherein Y is $CR^9R^{10}$, $NR^{11}$, O, S, SO, $SO_2$, $SOR^{12}$, and $SO_2R^{13}$, a single bond, or double bond; and $X^1$ and $X^2$ are $(CR^{14}R^{15})_m$ and $(CR^{16}R^{17})_n$ respectively, wherein each of m and n is either 1, 2, or 3 such that the sum m+n is either 2, 3, 4, 5, or 6, and for each of the m and n methylene units of $X^1$ and $X^2$, each of $R^9$-$R^{17}$ is selected independently from the group consisting of: hydrogen, halo, cyano, nitro, thio, amino, carboxyl, formyl, and alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl) alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkycarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted. Each of $R^{20a}$-$R^{23b}$ is selected independently from the group consisting of: hydrogen, halo, cyano, nitro, thio, amino, carboxyl, formyl, and alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkylcarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkycarbonylthiooxy, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxyloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

In more specific embodiments of Compound 2, each of $R^{20a}$-$R^{23b}$ is hydrogen, thus making the ring morpholin-1-yl. In other more specific embodiments, one of $R^{21a}$ and $R^{21b}$ and one of $R^{22a}$ and $R^{22b}$ is methyl, and the remaining substituents are hydrogen, thus providing a set of diastereomers of the mopholinyl ring moiety. In still other more specific embodiments, one of $R^{21a}$ and $R^{21b}$ is carboxyl.

Returning the generic structure 2 above, still more specific embodiments having the general structure 2 include those for which m=n=2, defining compounds in which $R^3$ is a six-membered ring. In still more specific embodiments of Compound 2, m=n=2, and $R^1$ and $R^8$ are selected independently from the group consisting of hydrogen and optionally substituted alkyl, and still more specifically $R^1$ and $R^8$ are selected independently from the group consisting of hydrogen, optionally substituted methyl, and optionally substituted ethyl.

Among those embodiments having the general structure 2 for which m=n=2 and $R^1$ and $R^8$ are selected independently from the group consisting of hydrogen, optionally substituted methyl, and optionally substituted ethyl, are those for which Y is O, defining thereby compounds in which $R^6$ is optionally substituted morpholin-1-yl. Such compounds are described by the general formula:

3

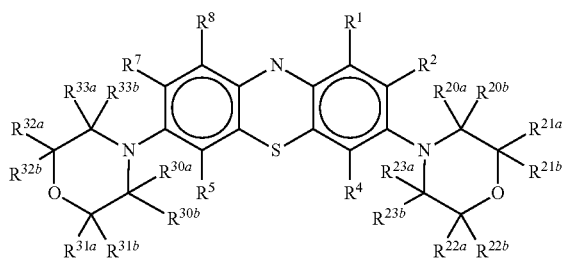

Each the substituents is defined as above for Compound 2, and each of $R^{30a}$-$R^{33b}$ is selected independently from the group consisting of: hydrogen, halo, cyano, nitro, thio, amino, carboxyl, formyl, and alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkycarbonylthiooxy, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

In more specific embodiments of Compound 3, each of $R^{30a}$-$R^{33b}$ is hydrogen, thus making the ring morpholin-1-yl. In other more specific embodiments, one of $R^{31a}$ and $R^{31b}$ and one of $R^{32a}$ and $R^{32b}$ is methyl, and the remaining substituents are hydrogen, thus providing a set of diastereomers of the mopholinyl ring moiety. In still other more specific embodiments, one of $R^{31a}$ and $R^{31b}$ is carboxyl.

Among those embodiments having the general structure 2 for which m=n=2 and $R^1$ and $R^8$ are selected independently from the group consisting of hydrogen, optionally substituted methyl, and optionally substituted ethyl, are those for which Y is $NR^{11}$, defining thereby compounds in which $R^6$ is optionally substituted piperazin-1-yl. Such compounds are described by the general formula:

4

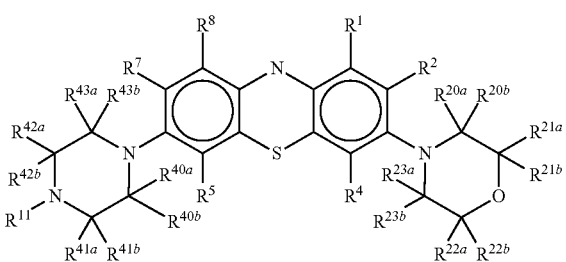

Each of the substituents is defined as above for Compound 2, and each of $R^{40a}$-$R^{43b}$ is selected independently from the group consisting of: hydrogen, halo, cyano, nitro, thio, amino, carboxyl, formyl, and alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkyloxycarbonyloxycarbonyl, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

In more specific embodiments of Compound 4, $R^{11}$ and each of $R^{40a}$-$R^{43b}$ is hydrogen, thus making the ring piperazin-1-yl. In other more specific embodiments, of Compound 4, $R^{11}$ is tert-butoxycarbonyl ("boc") and each of $R^{40a}$-$R^{43b}$ is hydrogen. In still other more specific embodiments, of Compound 4, $R^{11}$ is (tertbutylamino)carbonyl and each of $R^{40a}$-$R^{43b}$ is hydrogen.

Among those embodiments having the general structure 2 for which m=n=2 and $R^1$ and $R^8$ are selected independently from the group consisting of hydrogen, optionally substituted methyl, and optionally substituted ethyl, are those for which Y is $CR^9R^{10}$, defining thereby compounds in which $R^6$ is optionally substituted piperidin-1-yl. Such compounds are described by the general formula:

sulfonyl, heteroarylsulfonyl, cycloalkylsulfonyl, aralkyloxycarbonyloxycarbonyl, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

In more specific embodiments of Compound 5, $R^9$, $R^{10}$ and each of $R^{50a}$-$R^{53b}$ is hydrogen, thus making the ring piperidin-1-yl. In other more specific embodiments, $R^9$, $R^{10}$ are each fluorine and each of $R^{50a}$-$R^{53b}$ is hydrogen, thus making the ring 4,4-difluoropiperidin-1-yl. In still other more specific embodiments, one of $R^9$ and $R^{10}$ is dimethylamino, and the other and each of $R^{50a}$-$R^{53b}$ is hydrogen, thus making the ring 4-(dimethylamino)piperidin-1-yl. In yet other more specific embodiments, $R^9$ and $R^{10}$ are hydrogen, one of $R^{50a}$ and $R^{53a}$ is aminocarbonyl, and each of the reamining moieties $R^{50a}$-$R^{53b}$ is hydrogen.

Among those embodiments having the general structure 2 for which m=n=2 and $R^1$ and $R^8$ are selected independently from the group consisting of hydrogen, optionally substituted methyl, and optionally substituted ethyl, are those for which Y is S, defining thereby compounds in which $R^6$ is optionally substituted piperidin-1-yl. Such compounds are described by the general formula:

5

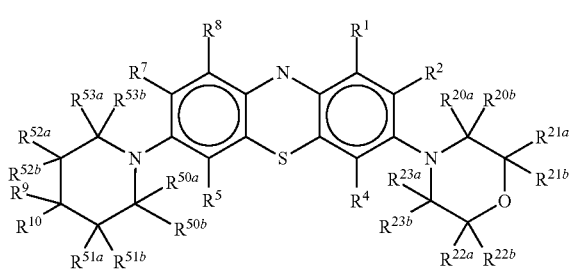

6

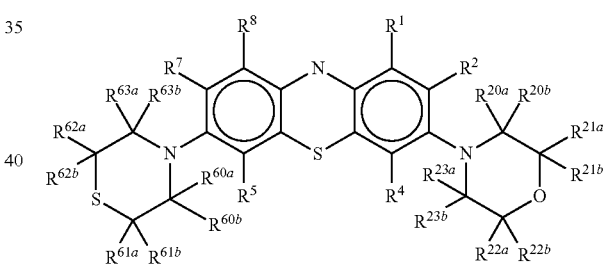

Each of the substituents is defined as above for Compound 2, and each of $R^{50a}$-$R^{53b}$ is selected independently from the group consisting of: hydrogen, halo, cyano, nitro, thio, amino, carboxyl, formyl, and alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, Each of the substituents is defined as above for Compound 2, and each of $R^{60a}$-$R^{63b}$ is selected independently from the group consisting of: hydrogen, halo, cyano, nitro, thio, amino, carboxyl, formyl, and alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkyloxycarbonyloxycarbonyl, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

In more specific embodiments of Compound 6, each of $R^{60a}$-$R^{63b}$ is hydrogen, thus making the ring thiomorpholin-1-yl.

Among those embodiments having the general structure 2 for which m=n=2 and $R^1$ and $R^8$ are selected independently from the group consisting of hydrogen, optionally substituted methyl, and optionally substituted ethyl, are those for which Y is a single bond, defining thereby compounds in which $R^6$ is optionally substituted pyrrolidin-1-yl. Such compounds are described by the general formula:

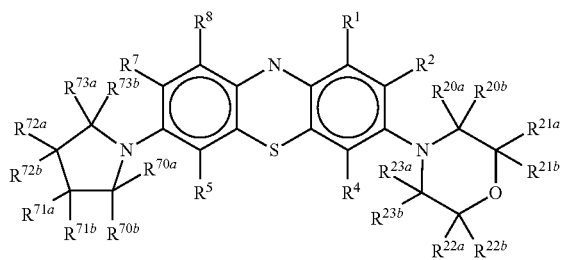

7

Each of where the substituents are defined as above for Compound 2, and each of $R^{70a}$-$R^{73b}$ is selected independently from the group consisting of: hydrogen, halo, cyano, nitro, thio, amino, carboxyl, formyl, and alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkyloxycarbonyloxycarbonyl, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

In more specific embodiments of Compound 7, each of $R^{70a}$-$R^{73b}$ is hydrogen, thus making the ring pyrrolidin-1-yl.

Among those embodiments having the general structure 2 for which m=2, n=3, and $R^1$ and $R^8$ are selected independently from the group consisting of hydrogen, optionally substituted methyl, and optionally substituted ethyl, are those for which Y is $NR^{11}$, defining thereby compounds in which $R^6$ is optionally substituted 1,4-diazepan-1-yl. Such compounds are described by the general formula:

8

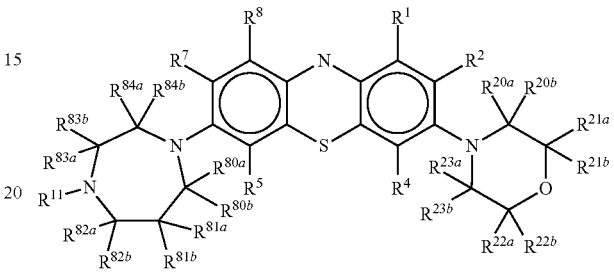

Each of where the substituents are defined as above for Compound 2, and each of $R^{80a}$-$R^{84b}$ is selected independently from the group consisting of: hydrogen, halo, cyano, nitro, thio, amino, carboxyl, formyl, and alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkyloxycarbonyloxycarbonyl, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

In more specific embodiments of Compound 8, $R^{11}$ and each of $R^{80a}$-$R^{84b}$ is hydrogen, thus making the ring 1,4-diazepan-1-yl. In other more specific embodiments, $R^{80a}$-$R^{84b}$ is hydrogen, and $R^{11}$ is boc. In still other more specific embodiments, $R^{80a}$-$R^{84b}$ is hydrogen, and $R^{11}$ is 2-propylsulfonyl.

Among those embodiments having the general structure 2 are those for which m=n=1 and $R^1$ and $R^8$ are selected independently from the group consisting of hydrogen, optionally substituted methyl, and optionally substituted ethyl, are those for which Y is a single bond, defining thereby compounds in which $R^6$ is optionally substituted azetidin-1-yl. Such compounds are described by the general formula:

9

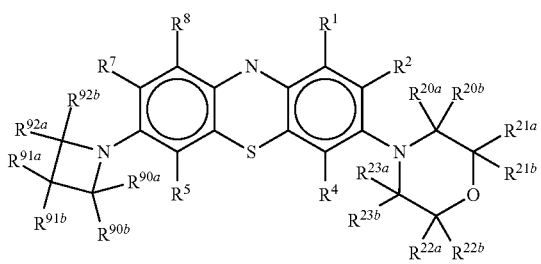

Each of where the substituents are defined as above for Compound 2, and each of $R^{90a}$-$R^{92b}$ is selected independently from the group consisting of: hydrogen, halo, cyano, nitro, thio, amino, carboxyl, formyl, and alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkyloxycarbonyloxycarbonyl, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

In more specific embodiments of Compound 9, each of $R^{90a}$-$R^{92b}$ is hydrogen, thus making the ring azetidin-1-yl.

Among those embodiments having the general structure 2 are those for which m=n=1 and $R^1$ and $R^8$ are selected independently from the group consisting of hydrogen, optionally substituted methyl, and optionally substituted ethyl, are those for which Y is a single bond, defining thereby compounds in which $R^6$ is optionally substituted azetidin-1-yl. Such compounds are described by the general formula:

10

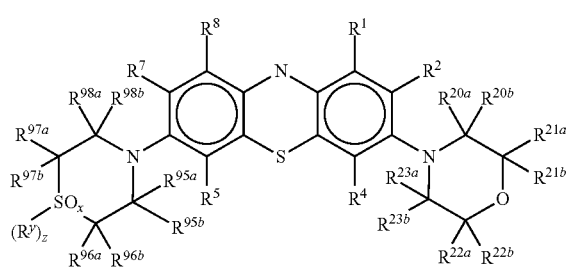

When z=1, the ring sulfur atom is substituted; when x=1, y=12, and when x=2, y=13, thus providing for substituted sulfinyl (i.e., $SOR^{11}$) and substituted sulfonyl (i.e., $SO_2R^{12}$) in the ring as described above with respect to Compound 2. When z=0, the sulfur is not substituted with an R-group (i.e., the ring sulfur is either sulfinyl (SO) or sulfonyl ($SO_2$)). Each of the remaining substituents are defined as above for Compound 2, and each of $R^{95a}$-$R^{98b}$ is selected independently from the group consisting of: hydrogen, halo, cyano, nitro, thio, amino, carboxyl, formyl, and alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkyloxycarbonyloxycarbonyl, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

In more specific embodiments of Compound 10, z=0, y=2, and each of $R^{95a}$-$R^{98b}$ is hydrogen.

In another aspect, the present invention provides methods and compositions for treating a viral disease in a mammal aicted with such disease, comprising administering to such mammal a therapeutically effective amount of a compound described herein. In more particular embodiments the viral disease is HIV, HCV, FLU, DENV, or VEEV. Particular, non limiting, exemplary compounds and their activites against these viruses are provided in the Appendix.

4.3 Synthesis of the Compounds of the Invention

The compounds of the present invention can be synthesized using techniques and materials known to those of skill in the art. Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Apin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.)

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography ("TLC"), recrystallization, distillation, high-pressure liquid chromatography ("HPLC") and the like. Also, various techniques well known in the chemical arts for the identification and quantification of chemical reaction products, such as proton and carbon-13 nuclear magnetic resonance CH and $^{13}$C NMR), infrared and ultraviolet spectroscopy ("IR" and "UV"), X-ray crystallography, elemental analysis ("EA"). HPLC and mass spectroscopy ("MS") can be used for identification, quantitation and purification as well.

Although the schemes below illustrate specific starting materials and products, those having ordinary skill in the art will understand that many substitution patterns can be made using known methods and materials in combination with the teachings herein.

Symmetrical compounds of the invention can be made using the transformations described in the following scheme:

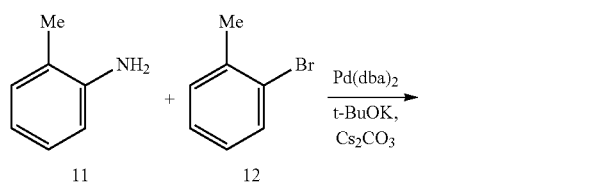

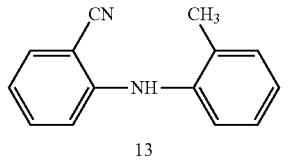

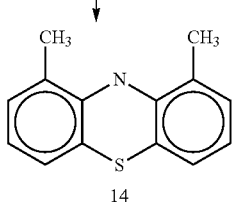

Starting from commercially available methylaniline (11) and bromotoluene (12), reaction with tris(dibenzylideneacetone)dipalladium(0), Pd(dba)$_2$ (or Pd$_2$(dba)$_3$), in suitable basic conditions, the coupled secondary amine 13. Subsequent reaction of that product with elemental sulfur and iodine provides the symmetrically substituted phenothiazine 14. Symmetrical bromination is achieved by reaction of 14 with bromine and acetic acid (below).

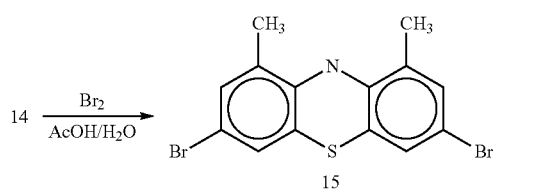

Reaction of the di-bromide with the desired piperazine in chloroform at room temperature provides the desired symmetrical amine.

Asymmetrical substitution patterns at the 1- and 9-positions of the parent ring can be made using the scheme below.

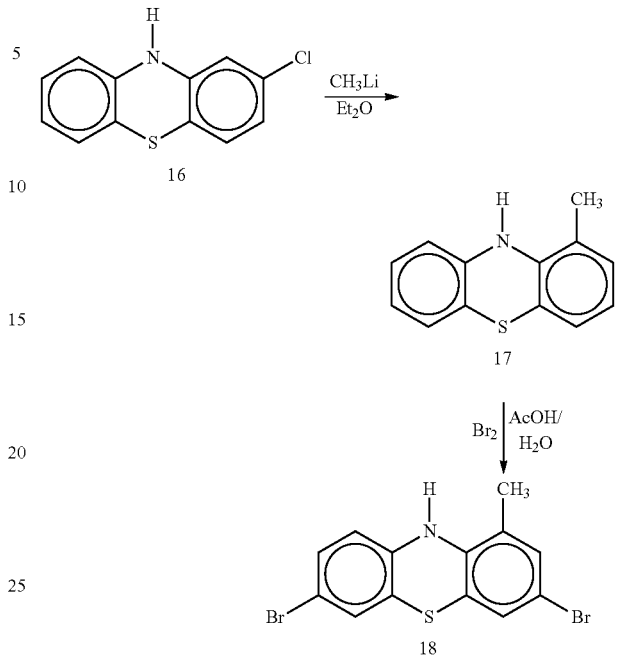

Starting from 2-chlorodiphenylthiazine (16), formation of the 1-methyl analog (17) is achieved reaction by reaction with methyllithium in diethylether. Reaction of that product with bromine in acetic acid and water provides the di-bromo adduct (18).

Reaction of the di-bromide with a chosen piperazine in chloroform at room temperature provides the desired bis(3, 6-piperazine).

Routes to asymmetrical substitutions at the 3- and 6-positions can be made using the following scheme (Y is O or N):

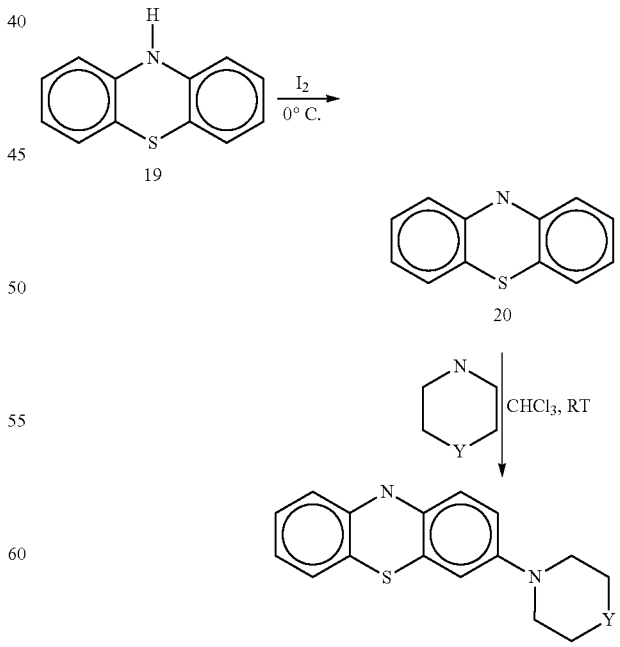

Reaction of 20 with a piperazine in chloroform at room temperature provides the desired amine 21.

Reaction of 21 with pyrrolidine and cesium carbonate (Cs$_2$CO$_3$) in dimethyl formamide at room temperature provides the desired asymmetical diamine 22 (Y is O or N):

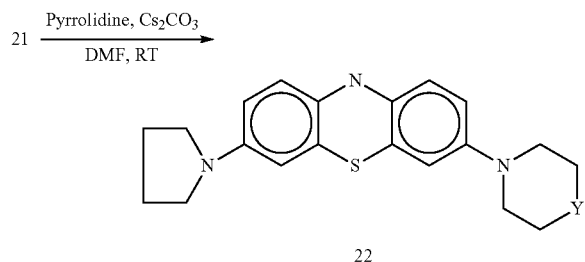

Compounds having an oxo substituent on the ring at R$^3$ or R$^6$ can be made by reaction of 21 with 8 M KOH in dioxane at room temperature provides the desired asymmetical diamine 23 (Y is O or N):

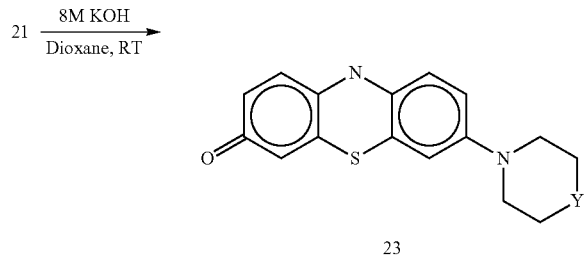

4.4 Methods for Treating Viral Diseases

In another aspect, the present invention provides methods for treating a viral disease in a mammal afflicted with such disease. In some embodiments, the methods provided by the invention comprise administering to such mammal a therapeutically effective amount of a compound having the structure of Compound 1 above, including any of the compounds disclosed herein. The formulation and provision of suitable pharmaceutical compositions will be understood by those having ordinary skill in the art. Viruses that can be treated using the compounds of the invention include, but are not limited to, Flu, HCV, HIV, EBOV, MARB, DENV, JUNV, YFV, VEEV, CHIKV, and WNV. In some embodiments, the virus is Ebola virus; in other embodiments, the virus is Marburg virus; and in still other embodiments, the virus is HIV.

4.5 Compositions for, and Methods of, Treating Viral Infections

Compounds of the present invention can be administered in a variety of ways including enteral, parenteral and topical routes of administration. For example, suitable modes of administration include oral, subcutaneous, transdermal, transmucosal, iontophoretic, intravenous, intramuscular, intraperitoneal, intranasal, subdural, rectal, vaginal, and the like.

In accordance with other embodiments of the present invention, there is provided a composition comprising a compound described here, together with a pharmaceutically acceptable carrier or excipient. Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in REMINGTON'S PHARMACEUTICAL SCIENCES, Mack Pub. Co., New Jersey (1991), which is incorporated herein by reference.

Pharmaceutical compositions of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compounds of the present invention may be administered orally, parenterally, sublingually, by inhalation spray, rectally, vaginally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid can be useful in the preparation of injectables.

Suppositories for rectal or vaginal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art.

While the compounds of the invention can be administered as the sole active pharmaceutical agent, they can also be used in combination with one or more other compound as described herein, or in combination with other agents used in the treatment or prevention of viral disease, or both.

In addition, the compounds of the present invention can be used, either singly or in combination as described above, in combination with other modalities for preventing or treating viral diseases or disorders. Such other treatment modalities include without limitation, surgery, radiation, hormone supplementation, and diet regulation. These can be performed sequentially (e.g., treatment with a compound of the invention following surgery or radiation) or in combination (e.g., in addition to a diet regimen).

In another aspect, the present invention provides methods for treating a viral disease in a mammal afflicted with such disease, comprising administering to such mammal a therapeutically effective amount of a compound among those described above with respect to Compound 1. In more particular embodiments the viral disease is Ebola virus. In other more particular embodiments, the viral disease is Marburg virus. Those having ordinary skill in the art will understand how to formulate and administer the compounds described herein.

In accordance with yet other embodiments, the present invention provides methods for treating or preventing viral disease in a human or animal subject in which an amount of a compound of the invention that is effective to at least ameliorate disease symptoms. Effective amounts of the compounds of the invention generally include any amount sufficient to detectably modulate a virus using standard measures, by other methods known to those having ordinary skill in the art, or by detecting prevention or alleviation of symptoms in a subject afflicted with a virus.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The prophylactically or therapeutically effective amount for a given situation can be readily determined by routine experimentation and is within the skill and judgment of the ordinary clinician.

For exemplary purposes of the present invention, a prophylactically or therapeutically effective dose will generally be from about 0.1 mg $kg^{-1}$ $d^{-1}$ to about 100 mg $kg^{-1}$ $d^{-1}$, preferably from about 1 mg $kg^{-1}$ $d^{-1}$ to about 20 mg $kg^{-1}$ $d^{-1}$, and most preferably from about 10 mg $kg^{-1}$ $d^{-1}$ to about 10 mg $kg^{-1}$ $d^{-1}$ of a compound of the present invention, which may be administered in one or multiple doses.

4.6 Examples

4.6.1 Synthesis of Compounds

The compounds of the present invention can be synthesized using techniques and materials known to those of skill in the art. Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Aspin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.)

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography ("TLC"), recrystallization, distillation, high-pressure liquid chromatography ("HPLC") and the like. Also, various techniques well known in the chemical arts for the identification and quantification of chemical reaction products, such as proton and carbon-13 nuclear magnetic resonance CH and $^{13}$C NMR), infrared and ultraviolet spectroscopy ("IR" and "UV"), X-ray crystallography, elemental analysis ("EA"). HPLC and mass spectroscopy ("MS") can be used for identification, quantitation and purification as well.

Although the schemes below illustrate specific starting materials and products, those having ordinary skill in the art will understand that many substitution patterns can be made using known methods and materials in combination with the teachings herein.

4.6.1.1 I. Synthesis of 1,9-Dimethylphenothiazin-5-ium a. Synthesis of Di-ortho-tolylamine

The round-bottom flask was heated then allow to cool to room temperature under argon. Added $Pd_2(dba)_3$ (1.39 g, 1.52 mmol, 1.0 mol %) or $Pd(dba)_2$ (1.38 g, 2.4 mmol, 1.4 mol %), 2-(di-tert-butylphosphino)biphenyl (1.09 g, 3.65 mmol, 2.4 mol %), 2-bromotoluene (40 mL, 332.1 mmol) or 2-chlorotoluene (39 mL, 332.1 mmol), lithium amide (3.47 g, 151.1 mmol, 45 mol %), sodium t-butoxide (29.5 g, 297.7 mmol, 90 mol %), followed by toluene (150 mL). The reaction mixture was heated at 80° C. under argon overnight, then allowed to cool to room temperature. Diluted with diethyl ether then filtered through a pad of Celite. Concentrated the resulting filtrate in vacuo. Used the crude material in the next reaction without purification. (Crude material can be purified by flash chromatography with hexane which gave the product as white crystals with a yellow tint (23.4 g, 118.6 mmol, 72% yield)).

b. Synthesis of 1,9-Dimethyl-10H-phenothiazine

Combined di(2-tolyl)amine (11.7 g, 59.3 mmol), elemental sulfur (3.9 g, 121.65 mmol, 2 eq.), crushed iodine (0.44 g, 1.73 mmol, 3 mol %) followed by o-dichlorobenzene (22 mL). Added an outlet to a dilute bleach solution (for hydrogen sulfide evolution) then put under argon. Re-fluxed at 180° C. for 4 hours then removed solvent under reduced pressure. Purified by column chromatography with 2.0% ethyl acetate/98% hexane to obtain product as white crystals (2 g, 8.8 mmol, 15% yield). Alternatively, the reaction was cooled to about 60° C. and hexane was added for extraction. Repeated hot hexane extractions of reaction until the product was no longer obtained in residue (about 4 times). Combined hexane extractions and concentrated in vacuo. Purified resulting residue either through repeated hot acetone/isopropanol crystallizations (or triturations) or flash chromatography using 2% ethyl acetate/98% hexane to obtain product as white crystals (2.92 g, 12.8 mmol, 28% yield).)

c. Synthesis of 1,9-Dimethylphenothiazin-5-ium iodide 1,9-Dimethylphenothiazine (4.2026 g, 18.49 mmol) was dissolved in 130 mL of chloroform and crushed iodine (14.1 g, 55.55 mmol, 3 eq.) dissolved in 520 mL of chloroform was added over 2 hurs. Once newly formed precipitate was filtered off or the solvent removed under vacuum, the resulting iodide salt was stirred with ether or hexane (sometimes overnight) to remove excess iodine then refiltered. After pumping down under vacuum, a brown precipitate was obtained as product (12.6 g).

4.6.1.2 II. Synthesis of 1-tert-Butylphenothiazin-5-ium a. Synthesis of 1-tert-Butyl-10H-phenothiazine Prepared 1-tert-Butyl-10H-phenothiazine as described in the literature starting from 2-chlorophenothiazine (3.09 g, 12.96 mmol) in THF (40 mL) with drop-wise addition of t-butyllithium solution in pentane (1.7 M in pentane, 38 mL, 64.6 mmol, 5 eq.). Alternatively, for the reaction, stirred for 2 hours then quenched with ice and a little ammonium chloride. After flash silica gel chromatography using an ethyl acetate-hexane gradient, the product was obtained as brown needled crystals (1.26 g, 4.9 mmol, 38% yield).

b. Synthesis of 1-tert-Butyl-phenothiazin-5-ium

This compound was prepared according the procedure by, B. Wilson et. al, *Tetrahedron* 64 (2008), 3429-3436. To the solution of 1-tert-butyl-10H-phenothiazine (0.660 g, 2.58 mmol) in chloroform (20 mL), at 5° C., was added a solution of iodine (1.98 g, 7.78 mmol) in $CHCl_3$ (80 mL) over a 1 h period. The resulting dark solution was stirred for an additional 1 h to overnight at 5° C., monitored by TLC. After the disappearance of the starting material, the cooling bath was removed. Solid precipitate was filtered, washed several times with hexane, then dried to afford a very dark solid as product (2.13 g, 35%).

4.6.1.3 III. Synthesis of 1-n-Butylphenothiazin-5-ium derivatives

Example 1

Synthesis of 3,7-Dimorpholino-1-n-butylphenothiazin-5-ium iodide a. 1-n-Butyl-10H-phenothiazine to a solution of 2-chloro-10H-phenothiazine (1.17 g, 5.0 mmol) in anhydrous ether (50 mL) n-butyl lithium (10 mL, 25 mmol, 2.5 M solution in hexane) was added dropwise for 1 h at room temperature. After that mixture had been stirred for 6 h, ice-water was added and the stirring was continued for 30 min. The organic layer was separated and combined with ether extracts of the aqueous phase. The combined organic phases were washed with water, dried ($Na_2SO_4$) and concentrated to give the product (0.9 g, 71%).

b. 1-n-butylphenothiazin-5-ium tetraiodide hydrate 1-n-butyl-10H-phenothiazine (700 mg, 2.75 mmol) was dissolved in chloroform (20 mL) and a solution of iodine (2.09 g, 8.25 mmol) also in chloroform (80 mL) was added to it drop wise at 5° C. for 4 h with vigorous stirring. Reaction progress was monitored by TLC. Black color precipitate was filtered, washed with copious amount of chloroform, dried under vacuum to afford product.

c. 3,7-Dimorpholino-1-n-butylphenothiazin-5-ium iodide to the stirred solution of 1-n-butylphenothiazin-5-ium tetraiodide hydrate (390 mg, 0.5 mmol) in acetonitrile (10 mL) morpholine (174 mg, 2.0 mmol) was added all at once with vigorous stirring at room temperature. The resulting mixture was stirred at room temperature 3 h, concentrated to dryness. The crude product was purified by flash chromatography (with methanol-chloroform) to provide the title compound.

Example 2

Preparation of Ethyl 4-[7-(dimethylamino)-1,9-dimethyl-phenothiazin-5-ium-3-yl]morpholine-2-carboxylate iodide and 4-[7-(dimethylamino)-1,9-dimethyl-phenothiazin-5-ium-3-yl]morpholine-2-carboxylic acid iodide a. Synthesis of 3-Aminophenothiazin-5-ium Triiodide The dimethylphenothiazin-5-ium salt (0.850 g, 1.13 mmol) was dissolved or suspended in $CHCl_3$ (40 mL). Ethyl morpholine-2-carboxylate (0.38 g, 2.32 mmol, 2 eq.) in $CHCl_3$ was added dropwise. The mixture was stirred at 0° C. for 2 h, monitored by TLC. The solvent was decanted and the solid was washed with hexane overnight. The crude material was used without purification.

b. Synthesis of Ethyl 4-[7-(dimethylamino)-1,9-dimethyl-phenothiazin-5-ium-3-yl]morpholine-2-carboxylate iodide and 4-[7-(dimethylamino)-1,9-dimethyl-phenothiazin-5-ium-3-yl]morpholine-2-carboxylic acid iodide The crude product isolated from the previous step was dissolved in acetonitrile (16 mL). Dimethylamine solution (2

M in THF; 0.330 mL, 165 mmol) was added to the reaction drop-wise. The reaction was monitored by TLC and LC/MS. When the reaction was completed (overnight), it was concentrated to dryness. The residue was purified by flash chromatography, using a methanol-chloroform gradient, to obtain the product and the acid by-product.

EXAMPLES 1. 4-[7-(Azetidin-1-yl)-1,9-dimethyl-phenothiazin-5-ium-3-yl]morpholine iodide: The compound was synthesized as in example above.
2. 4-(1,9-Dimethyl-7-thiomorpholino-phenothiazin-5-ium-3-yl)morpholine iodide: The compound was synthesized as in example above.
3. 4-(1,9-Dimethyl-7-morpholino-phenothiazin-5-ium-3-yl)piperazine-1-sulfonamide iodide: The compound was synthesized as in example above.
4. 4-[7-[(2S,6R)-2,6-Dimethylmorpholin-4-yl]-1,9-dimethyl-phenothiazin-5-ium-3-yl]-piperazine-1-sulfonamide iodide: The compound was synthesized as in example above.
5. 4-[7-[(2R,6R)-2,6-Dimethylmorpholin-4-yl]-1,9-dimethyl-phenothiazin-5-ium-3-yl]-piperazine-1-sulfonamide iodide: The compound was synthesized as in example above.
6. (2R,6S)-4-[7-[(2R,6S)-2,6-Dimethylmorpholin-4-yl]-1,9-dimethyl-phenothiazin-5-ium-3-yl]-2,6-dimethyl-morpholine iodide: The compound was synthesized as in example above.
7. (2R,6S)-4-[7-[(2R,6R)-2,6-dimethyl-morpholin-4-yl]-1,9-dimethyl-phenothiazin-5-ium-3-yl]-2,6-dimethyl-morpholine iodide: The compound was synthesized as in example above.
8. (2R,6S)-4-(1,9-Dimethyl-7-morpholino-phenothiazin-5-ium-3-yl)-2,6-dimethyl-morpholine iodide: The compound was synthesized as in example above.
9. (2S,6S)-4-(1,9-Dimethyl-7-morpholino-phenothiazin-5-ium-3-yl)-2,6-dimethyl-morpholine iodide: The compound was synthesized as in example above.
10. tert-Butyl 4-(1,9-dimethyl-7-morpholino-phenothiazin-5-ium-3-yl)piperazine-1-carboxylate iodide: The compound was synthesized as in example above.
11. 4-(1,9-Dimethyl-7-piperazin-1-yl-phenothiazin-5-ium-3-yl)morpholine iodide: The compound was synthesized as in example above and the Boc group was removed using acidic conditions.
12. 4-(1,9-Dimethyl-7-piperazin-1-yl-phenothiazin-5-ium-3-yl)morpholine chloride: The compound was synthesized as in example above and the Boc group was removed using acidic conditions.
13. 4-(1,9-Dimethyl-7-piperazin-1-yl-phenothiazin-5-ium-3-yl)morpholine 2,2,2-trifluoroacetate: The compound was synthesized as in example above and the Boc group was removed using acidic conditions.
14. 4-[1,9-Dimethyl-7-(4-methylpiperazin-1-yl)phenothiazin-5-ium-3-yl]morpholine iodide: The compound was synthesized as in example above.
15. 4-[7-[(4aR,8aS)-3,4,4a,5,6,7,8,8a-Octahydro-2H-quinolin-1-yl]-1,9-dimethyl-phenothiazin-5-ium-3-yl]morpholine iodide: The compound was synthesized as in example above.
16. 4-[7-(4,4-Difluoro-1-piperidyl)-1,9-dimethyl-phenothiazin-5-ium-3-yl]morpholine iodide: The compound was synthesized as in example above.
17. tert-Butyl 4-(1,9-dimethyl-7-morpholino-phenothiazin-5-ium-3-yl)-1,4-diazepane-1-carboxylate iodide: The compound was synthesized as in example above.
18. 4-[7-(1,4-Diazepan-1-yl)-1,9-dimethyl-phenothiazin-5-ium-3-yl]morpholine chloride: The compound was synthesized as in example above and the Boc group was removed using acidic conditions.
19. N-isopropyl-1,9-dimethyl-7-morpholino-phenothiazin-5-ium-3-amine iodide: The compound was synthesized as in example above.
20. 4-(1-tert-Butyl-7-morpholino-phenothiazin-5-ium-3-yl)morpholine iodide: The compound was synthesized as in example above.

Preparation of 1-(butan-2-yl)-phenothiazin-5-ium iodide

The stirred solution of 2-chlorophenothiazine (5.02 g, 21.54 mmol) in anhydrous THF (50 mL) was cooled to −78° C. and under argon sec-butyl lithium (77 mL, 108 mmol) was added drop-wise. After all the addition, the resulting orange mixture was stirred at −78° C. for 3 h, then was allowed to warm to room temperature. The reaction was quenched by the slow addition of saturated ammonium chloride, extracted with ethyl acetate (2×400 mL). The combined organics were washed with brine, dried (MgSO$_4$), filtered, concentrated, and purified by chromatography, using ethyl acetate-hexane gradient to afford 1-sec-butyl-10H-phenothiazine. MS (m/z): [M+H]$^+$=256. To the solution of 1-sec-butyl-10H-phenothiazine (1.0 g, 4.14 mmols) in chloroform (30 mL), at 5° C. was added the solution of iodine (3.2 g, 12.61 mmol) in chloroform (125 mL) drop-wise. After the addition the resulting dark mixture was stirred at 5° C. overnight. Product was filtered, washed several times with chloroform, dried to afford the title compound (1.8 g, 68%).

Preparation of 3-(4-(tert-butoxycarbonyl)-1,4-diazepan-1-yl-1-sec-butyl-7-morpholinophenthiazin-5-ium iodide To the solution of the previous product (0.3013 g, 0.46 mmol) in CHCl$_3$ (8 mL) was added the solution of boc-homopiperazine (204 g, 1.02 mmol) in CHCl$_3$ (2 mL). The resulting mixture was stirred at room temperature for 3 h and concentrated to dryness. The crude obtained was treated with MeOH (12 mL), morpholine (178 µL, 2.04 mmol) and stirred at room temperature overnight. The reaction crude was purified by chromatography on the Teledyne Isco machine using MeOH/CHCl$_3$ gradient to afford the title compound. MS (m/z): [M+H]$^+$=538 (neutral product).

Preparation of 1-sec-butyl-3-(1,4-diazepan-1-yl)-7-morpholinophenothiazin-6-ium chloride To 3-(4-(tert-butoxycarbonyl)-1,4-diazepan-1-yl-1-sec-butyl-7-morpholinophenthiazin-5-ium iodide in anhydrous 1,2-dichloroethane (5 mL) was added 4 M HCl-in-Dioxane (5 mL). The resulting solution was stirred at room temperature overnight, concentrated to dryness. The residue obtained was triturated with ether and re-concentrated to dryness to afford the title compound. MS (m/z): [M+H]+=438.

Preparation of 1-sec-butyl-3-(4-(tert-butylcarbamoyl)-1,4-diazepan-1-yl)-7-morpholinophenathiazin-5-ium iodide To the solution of 4-(1-tert-Butyl-7-morpholino-phenothiazin-5-ium-3-yl)morpholine iodide was (0.38 g, 0.58 mmol)

in CHCl₃ (10 mL) was added the mixture of N-tert-butyl-1,4-diazepane-1-carboxamide hydrochloride 6 (0.302 g, 1.28 mmol), triethylamine (337 μL, 2.43 mmol) in CHCl₃ (5 mL). The resulting mixture was stirred at room temperature overnight, then concentrated to dryness. MeOH (15 mL) and morpholine (312 μL, 3.56 mmol) was added to the crude obtained and stirred at room temperature overnight. Purification of the crude by chromatography using MeOH/CHCl₃ gradient afforded the title compound. MS (m/z): [M+H]⁺=538 (neutral compound).

Preparation of 1-sec-butyl-3-(4-(isopropylsulfonyl)-1,4-diazepan-1yl)-7-morpholinophenothiazin-5-ium iodide The compound was prepared analogously as example above with 1-(isopropylsulfonyl)-1,4-diazepane hydrochloride employed for the first substitution step. MS (m/z): [M+H]⁺=545.

Preparation of 1-sec-butyl-3-(4-(cyclopropylsulfonyl)-1,4-diazepan-1yl)-7-morpholinohenothiazin-5-ium iodide 1-sec-Butyl-3-(4-(cyclopropylsulfonyl)-1,4-diazepan-1yl)-7-morpholinophenothiazin-5-ium iodide was prepared analogously as described above, employing 1-(cyclopropylsulfonyl)-1,4-diazepane hydrochloride and morpholine. MS (m/z): [M+H]⁺=543.

Preparation of 1-sec-butyl-3-(4-(cyclopropylsulfonyl)piperazin-1yl)-7-morpholinophenothiazin-5-ium iodide 1-(cyclopropylsulfonyl)piperazine hydrochloride and morpholine were employed in the preparation of title compound. MS (m/z): [M+H]⁺=528.

Preparation of 1-sec-butyl-3,7-dimorpholinophenothiazin-5-ium iodide

Treatment of 1-sec-butylphenothiazin-5-ium tetraiodide hydrate with excess morpholine in CHCl₃ afforded the title compound. MS (m/z): [M+H]⁺=425.

Preparation of 3-(4-(tert-butoxycarbonyl)-1,4-diazepan-1-yl)-1-isopropyl-7-morpholinophenothiazin-5-ium iodide 1-Isopropylphenothiazin-5-ium tetraiodide hydrate was prepared as described above with isopropyllithium employed as the lithiation reagent. Treatment of the hydrate sequentially with boc-homopiperazine and morpholine afforded the title compound. MS (m/z): [M+H]⁺=524.

Preparation of 3-(1,4-diazepan-1yl)-1-isopropyl-7-morpholinophenothiazin-5-ium chloride Title compound was prepared as described above. MS (m/z): [M+H]+=424.

Preparation of 1-isopropyl-3,7-dimorpholinophenothiazin-5-ium iodide

Title compound was prepared as described above. MS (m/z): [M+H]+=411.

Preparation of 1,9-diethyl-3-morpholino-7-(4-sulfamoylpiperazin-1-yl)phenothiazin-5-ium iodide To the solution of 1,9-diethylphenothiazin-5-ium tetraiodide hydrate (0.226 g, 0.35 mmol) in CHCl₃ (10 mL) was added the mixture of piperazine-1-sulfonamide hydrochloride (0.14 g, 0.7 mmol), triethylamine (200 μL, 1.44 mmol). The resulting mixture was stirred at room temperature for 3 h and concentrated to dryness. The crude obtained was treated with MeOH and morpholine as described above to furnish the title compound. MS (m/z): [M+H]+=503

Preparation of 3-(3-carbamoylpiperidin-1-yl)-1,9-diethyl-7-morpholinophenothiazin-5-ium iodide Sequential treatment of 1,9-diethylphenothiazin-5-ium tetraiodide hydrate with nipecotamide in CHCl₃ and morpholine in MeOH afforded the title compound. MS (m/z): [M+H]+=466.

Preparation of 3-(4-(tert-butoxycarbonyl)-3-(methoxycarbonyl)piperazin-1yl)-1,9-diethyl-7-morpholinophenothiazin-5-ium iodide Title compound was prepared as described for the above compound with N-1-boc-2-piperazinecarboxylic acid methyl ester substituted for the first step, followed by morpholine in MeOH to afford the title compound. MS (m/z): [M+H]+=582.

Preparation of 1,9-diethyl-3-morpholino-7-(4-(trifluoromethylsulfonamido)piperidin-1-yl)phenothiazin-5-ium iodide Title compound was prepared by the sequential treatment of 1,9-diethylphenothiazin-5-ium tetraiodide hydrate with 1,1,1 trifluoro-N-(piperidin-4-yl)methanesulfonamide hydrochloride and triethylamine in CHCl₃ followed by morpholine in MeOH to afford the desired compound. MS (m/z): [M+H]⁺=570.

Preparation of 1,9-diethyl-3-(4-(1-methylethylsulfonamido)piperidine-1-yl)-7-morpholinophenothiazin-5-ium iodide Title compound was prepared as described above with N-(piperidin-4-yl)propane-2-sulfonamide hydrochloride used in the first substitution reaction to afford the desired compound. MS (m/z): [M+H]⁺=544.

Preparation of 3-(4-cyanopiperidin-1-yl)-1,9-diethyl-7-morpholinophenothiazin-5-ium iodide Substitution of 1,9-diethylphenothiazin-5-ium tetraiodide hydrate with 4-cyanopiperidine in CHCl₃ followed by the treatment of morpholine in methanol afforded the title compound. MS (M/z): [M+H]⁺=448.

Preparation of 3-(azetidin-1-yl)-1,9-diethyl-7-morpholinophenothiazin-5-ium iodide Sequential amination of 1,9-diethylphenothiazin-5-ium tetraiodide hydrate with azetidine hydrochloride, triethylamine in CHCl₃ followed by the usual treatment with morpholine afforded the title compound. MS (m/z): [M+H]+=395.

Preparation of 4-(1,9-diethyl-7-morpholino-phenothiazin-5-ium-3-yl)-1,4-thiazine 1,1-dioxide Treatment of 1,9-diethylphenothiazin-5-ium tetraiodide hydrate with thiomorpholine 1,1-dioxide in CHCl₃, then the usual reaction with morpholine afforded the title compound. MS (m/z): [M+H]+= 473.

Preparation of 3-(4-(cyclopropanesulfonamido)piperidin-1-yl)-1,9-diethyl-7-morpholinophenothiazin-5-ium iodide Title compound was prepared as described above with N-(piperidin-4-yl)cyclopropanesulfonamide hydrochloride substituted to produce the desired compound. MS (m/z): [M+H]$^+$=542.

Preparation of 1,9-diethyl-3-morpholino-7-(octahydroisoquinolin-2(1H)-yl)phenothiazin-5-ium iodide The titled compound was prepared by employing perhydroisoquinoline in the first substitution step followed by the usual with morpholine. MS (m/z): [M+H]$^+$=476.

Preparation of 1,9-diethyl-3-(2-(2-hydroxyethyl)piperidin-1-yl)-7-morpholinophenothiazin-5-ium iodide Title compound was prepared as described above with 2-piperidineethanol was employed in the first substitution step. MS (m/z): [M+H]$^+$=466.

Preparation of 1,9-diethyl-3-morpholino-7-((4Ar,8aS)-octahydroquinolin-1(12H)-yl)phenothiazin-5-ium iodide Treatment of 1,9-diethylphenothiazin-5-ium tetraiodide hydrate with trans-decahydroquinoline in CHCl₃ followed by the usual reaction with morpholine afforded the title compound. MS (m/z): [M+H]$^+$=476.

IV. 1-Ethyl-9-methylphenothiazinium-5-ium derivatives

Synthesis of 1-Ethyl-9-methylphenothia-zin-5-ium tetraiodide hydrate a. N-Acetyl-2-ethylaniline commercial 2-ethylaniline (50 mL, 0.40 mol) was dissolved in acetic anhydride (160 mL, 1.70 mol) and stirred at room temperature for 2 h. Then the reaction mixture was poured into H₂O, the whole was extracted with ethyl acetate (2×200 mL). The combined organic extracts were washed with 5% aqueous NaHCO₃, brine, dried (K₂CO₃), filtered and concentrated to provide the title compound as a white solid (60.0 g, 92%).

b. N-Acetyl-2-ethyl-2'-methyldiphenylamine

A mixture of the N-acetyl-2-ethylaniline (35.0 g, 215 mmol), anhydrous Cs₂CO₃ (70.0 g, 215 mmol), CuBr (2.86 g, 20 mmol), KI (3.33 g, 20 mmol) and 2-bromotoluene (3) (78 mL, 640 mmol) was stirred and heated at 175-180° C. under an argon atmosphere for 48 h. After cooling the reaction mixture was poured into ice-H₂O and extracted with ethyl acetate (2×200 mL), the combined organic extracts were washed with brine, dried over anhydrous K₂CO₃, filtered and concentrated to dryness. The obtained crude material was purified by flash chromatography (using ethyl acetate-hexane) to afford the N-acetyl-2-ethyl-2'-methyldiphenylamine (35.4 g, 65%).

c. 2-Ethyl-2'-methyldiphenylamine

A solution of the N-acetyl-2-ethyl-2'-methyldiphenylamine (32.5 g, 128 mmol) in 10% KOH (72 g, 1.28 mol)/EtOH (120 mL) was stirred and refluxed for 6 h, then poured into H₂O. The mixture was extracted with ethyl acetate (2×100 mL). The combined organic layers were washed with brine, dried (Na₂SO₄), filtered and concentrated to dryness, gave dark red oil (21.1 g, 78%).

d. 1-Ethyl-9-methyl-10H-phenothiazine

To a 2-ethyl-2'-methyldiphenylamine (3.0 g, 14.2 mmol), sulfur (909 mg, 28.4 mmol) and iodine (601 mg, 4.7 mmol) were added. Vial was charged with balloon for discharge. The heating block was preheated (150° C.). The vial was heated on the heating block and after 15 min. temperature was increased to 210° C., reaction mixture was stirred and heated for an additional 1 h. The mixture was allowed to cool to 90° C. The dark solid material was dissolved in mixture methanol/chloroform and purified by flash chromatography (ethyl acetate-hexane) to afford the desired product (790 mg, 23%).

e. 1-Ethyl-9-methylphenothiazin-5-ium tetraiodide hydrate

A solution of 1-ethyl-9-methyl-10H-phenothiazine (4.83 g, 20 mmol) in anhydrous chloroform (50 mL) was stirred at 5° C. and the solution of iodine (15.25 g, 60 mmol) in CHCl₃ (300 mL) was added drop wise over 3 h. The resulting dark solution was stirred for an additional 3 h at 5° C., monitored by TLC. After the disappearance of the starting material, the resulting precipitate was filtered, washed with a copious amount of chloroform, dried overnight in vacuum to afford a dark solid (9.18 g, 60%).

V. Synthesis of 1-Ethyl-9-methyl-7-morpholino-3-(piperazin-1-yl)phenothiazin-5-ium trifluoroacetate a. 3-(4-Boc-piperazin-1-yl)-1-ethyl-9-methyl-phenothiazin-5-ium triiodide To the stirred mixture of 9-ethyl-1-methylphenothiazin-5-ium tetraiodide hydrate (383 mg, 0.5 mmol) in anhydrous CHCl₃ (20 mL) 1-Boc-piperazine (93 mg, 0.5 mmol) was added drop wise over 4 h. The resulting mixture was stirred at room temperature overnight, concentrated to dryness.

b. 3-(4-Boc-piperazin-1-yl)-1-ethyl-9-methyl-7-morpholino-phenothiazin-5-ium iodide A solution of 3-(4-Boc-piperazin-1-yl)-1-ethyl-9-methylphenothiazin-5-ium triiodide (403 mg, 0.5 mmol) in acetonitrile (10 mL) and morpholine (70 mg, 0.8 mmol) was stirred for 4 h at 50° C. The resulting mixture was concentrated to dryness and purified by flash chromatography using the methanol-chloroform gradient.

c. 1-ethyl-9-methyl-7-morpholino-3-(piperazin-1-yl)-phenothiazin-5-ium trifluoroacetate A solution of 3-(4-Boc-piperazin-1-yl)-1-ethyl-9-methyl-7-morpholinophenothiazin-5-ium iodide (65 mg, 0.01 mmol) in dichloromethane (10 mL) and trifluoroacetic acid (1.0 mL) was stirred for 1 h at 50° C. The resulting mixture was washed by toluene (2×5 mL), pentane (2×5 mL) and concentrated to dryness.

VI. Synthesis of 1-Ethyl-9-methyl-7-morpholi-no-3-(thiomorpholin-4,4-dioxide-1-yl)phenothiazin-5-ium iodide a. 1-Ethyl-9-methyl-7-(morpholin-1yl)phenothiazin-5-ium triiodide

To the stirred mixture of 1-ethyl-9-methylphenothiazin-5-ium tetraiodide hydrate (1.53 g, 2.0 mmol) in anhydrous CHCl$_3$ (20 mL) morpholine (0.18 mL, 2.0 mmol) was added drop wise over 1 h. The resulting mixture was stirred at room temperature overnight, concentrated to dryness.

b. 1-Ethyl-9-methyl-7-morpholino-3-(thiomorpholin-4,4-dioxide-1-yl)phenothiazin-5-ium iodide A solution of 1-ethyl-9-methyl-7-(morpholin-1yl)phenothiazin-5-ium triiodide (353 mg, 0.5 mmol) in acetonitrile (10 mL) and thiomorpholine-1,1-dioxide (95.6 mg, 0.7 mmol) was stirred for 4 h at 50° C. The resulting mixture was concentrated to dryness and purified by flash chromatography using the methanol-chloroform gradient.

VII. Synthesis of 1-Ethyl-9-methyl-3-(dimethylamino)-7-(3,5-dimethylmorpholin-1-yl)phenothiazin-5-ium iodide a. 1-Ethyl-9-methyl-3-(dimethylamino)phenothiazin-5-ium triiodide

To the stirred mixture of 1-ethyl-9-methylphenothiazin-5-ium tetraiodide hydrate (383 mg, 0.5 mmol) in anhydrous CHCl$_3$ (20 mL) dimethylamine (0.5 mL, 1.0 mmol, 2 m solution in THF) was added drop wise over 4 h. The resulting mixture was stirred at room temperature overnight, concentrated to dryness.

b. 1-Ethyl-9-methyl-3-(dimethylamino)-7-(3,5-dimethylmorpholin-1-yl)phenothiazin-5-ium iodide a solution of 1-ethyl-9-methyl-3-(dimethylamino)-phenothiazin-5-ium triiodide (137 mg, 0.21 mmol) in methanol (10 mL) and 3,5-dimethylaminomorpholine (80 mg, 0.7 mmol) was stirred for 2 h at room temperature. The resulting mixture was concentrated to dryness and purified by flash chromatography using the methanol-chloroform gradient to provide the title compound.

VIII. Synthesis of 1-Ethyl-9-methyl-3,7-bis(3,5-dimethyl-morpholin-1-yl)phenothiazin-5-ium iodide a. 1-Ethyl-9-methyl-3,7-bis(3,5-dimethylmorpholin-1-yl)phenothiazin-5-ium iodide A solution of 1-ethyl-9-methylphenothiazin-5-ium tetraiodide hydrate (76 mg, 0.1 mmol) in mixture methanol-acetonytrile (1:1) (10 mL) and 3,5-dimethylaminomorpholine (115 mg, 1.0 mmol) was stirred for 4 h at room temperature. The resulting mixture was concentrated to dryness and purified by flash chromatography using the methanol-chloroform gradient to provide the title compound.

IX. Synthesis of 1-Ethyl-9-methyl-3,7-bis(2,6-dimethylmorpholin-1-yl)phenothiazin-5-ium iodide a. 1-Ethyl-9-methyl-3,7-bis(2,6-dimethylmorpholin-1-yl)phenothiazin-5-ium iodide A solution of 1-ethyl-9-methylphenothiazin-5-ium tetraiodide hydrate (228 mg, 0.3 mmol) in mixture methanol-acetonytrile (1:1) (20 mL) and 2,6-dimethylaminomorpholine (230 mg, 2.0 mmol) was stirred for 3 h at room temperature. The resulting mixture was concentrated to dryness and purified by flash chromatography using the methanol-chloroform gradient to provide the title compound.

X. Synthesis of 1-Ethyl-9-methyl-3-(dimethylamino)-7-(2,6-dimethylmorpholin-1-yl)phenothiazin-5-ium iodide a. 1-Ethyl-9-methyl-3-(dimethylamino)phenothiazin-5-ium triiodide

To the stirred mixture of 1-ethyl-9-methylphenothiazin-5-ium tetraiodide hydrate (383 mg, 0.5 mmol) in anhydrous CHCl$_3$ (20 mL) dimethylamine (0.5 mL, 1.0 mmol, 2 M solution in THF) was added drop wise over 4 h. The resulting mixture was stirred at room temperature overnight, concentrated to dryness.

b. 1-Ethyl-9-methyl-3-(dimethylamino)-7-(2,6-dimethylmorpholin-1-yl)phenothiazin-5-ium iodide a solution of 1-ethyl-9-methyl-3-(dimethylamino)-phenothiazin-5-ium triiodide (270 mg, 0.4 mmol) in methanol (10 mL) and 2,6-dimethylaminomorpholine (160 mg, 1.4 mmol) was stirred for 2 h at room temperature. The resulting mixture was concentrated to dryness and purified by flash chromatography using the methanol-chloroform gradient to provide the title compound.

XI. Synthesis of 1-Ethyl-9-methyl-3-morpholi-no-7-(4-(di-methylamino)piperidin-1-yl)phenothiazin-5-ium iodide a. 1-Ethyl-9-methyl-3-(morpholin-1yl)phenothiazin-5-ium triiodide

To the stirred mixture of 1-ethyl-9-methylphenothiazin-5-ium tetraiodide hydrate (1.53 g, 2.0 mmol) in anhydrous CHCl$_3$ (20 mL) morpholine (0.18 mL, 2.0 mmol) was added drop wise over 1 h. The resulting mixture was stirred at room temperature overnight, concentrated to dryness.

b. 1-Ethyl-9-methyl-3-morpholino-7-(4-(dimethylamino)piperidin-1-yl)phenothiazin-5-ium iodide A solution of 1-ethyl-9-methyl-7-(morpholin-1yl)phenothiazin-5-ium triiodide (120 mg, 0.17 mmol) in methanol (10 mL) and 4-(dimethylamino)piperidine (64 mg, 0.5 mmol) was stirred for 4 h at room temperature. The resulting mixture was concentrated to dryness and purified by flash chromatography using the methanol-chloroform gradient.

XII. Synthesis of 1-Ethyl-9-methyl-7-morpholi-no-3-(4-(N-Boc-amino)piperidin-1-yl)phenothiazin-5-ium iodide a. 1-Ethyl-9-methyl-3-(4-N-Boc-amino)piperidin-1yl)phenothiazin-5-ium triiodide To the stirred mixture of 1-ethyl-9-methylphenothiazin-5-ium tetraiodide hydrate (153 mg, 0.2 mmol) in anhydrous $CHCl_3$ (10 mL) 4-N-Boc-aminopiperidine (60 mg, 0.3 mmol) was added with stirring. The resulting mixture was stirred at room temperature overnight, concentrated to dryness.

b. 1-Ethyl-9-methyl-7-morpholino-3-(4-N-Boc-amino)piperidin-1-yl)phenothiazin-5-ium iodide A solution of 1-ethyl-9-methyl-3-(4-N-Boc-amino)piperidin-1yl)phenothiazin-5-ium triiodide (165 mg, 0.2 mmol) in methanol (10 mL) and morpholine (17.4 mg, 0.2 mmol) was stirred for 4 h at room temperature. The resulting mixture was concentrated to dryness and purified by flash chromatography using the methanol-chloroform gradient and prep-chromatography.

XIII. Synthesis of 1-Ethyl-9-methyl-7-morpholi-no-3-(4-aminopiperidin-1-yl)phenothiazin-5-ium trifluoroace-tate a. 1-Ethyl-9-methyl-7-morpholino-3-(4-aminopiperidin-1-yl)phenothiazin-5-ium trifluoroacetate 1-Ethyl-9-methyl-7-morpholino-3-(4-N-Boc-amino)piperidin-1yl)phenothiazin-5-ium iodide (65 mg, 0.1 mmol) was dissolved in dichloromethane (5 mL) and trifluoroacetic acid (1.0 mL) was added to it at room temperature. Reaction mixture was stirred 3 h at 50° C. The resulting mixture was concentrated, washed with toluene, pentane and dried under vacuum.

XIV. Synthesis of 1-Ethyl-9-methyl-7-morpholi-no-3-(4-N-Boc-1,4-diazepane-1-yl)phenothiazin-5-ium iodide a. 1-Ethyl-9-methyl-3-(4-N-Boc-1,4-diazepane-1-yl)phenothiazin-5-ium triiodide To the stirred mixture of 1-ethyl-9-methylphenothiazin-5-ium tetraiodide hydrate (780 mg, 1.0 mmol) (7) in anhydrous $CHCl_3$ (15 mL) 1-Boc-1,4-diazepane (400 mg, 2.0 mmol) was added at room temperature. The resulting mixture was stirred at this temperature for 4 h. Solvent was removed under vacuum.

b. 1-Ethyl-9-methyl-7-morpholino-3-(4-Boc-1,4-diazepane-1-yl)-phenothiazin-5-ium iodide A solution of 1-ethyl-9-methyl-3-(4-Boc-1,4-diazepane-1-yl)phenothiazin-5-ium triiodide (165 mg, 0.2 mmol) in acetonitrile (10 mL) and morpholine (70 mg, 0.8 mmol) was stirred for 4 h at room temperature. The resulting mixture was concentrated to dryness and purified by flash chromatography using the methanol-chloroform gradient.

XV. 1-Ethyl-9-methyl-7-morpholino-3-(1,4-diazepane-1-yl)phenothiazin-5-ium chloride a. 1-Ethyl-9-methyl-7-morpholino-3-(1,4-diazepane-1-yl)phenothiazin-5-ium chloride A solution of 1-ethyl-9-methyl-7-morpholino-3-(4-Boc-1,4-diazepane-1-yl)phenothiazin-5-ium iodide (65 mg, 0.1 mmol) in dichloromethane (10 mL) and HCl (1.0 mL, 4 M solution in 1,4-dioxane) was stirred for 2 h at 50° C. Product was precipitated, liquid was decanted. Solid material was dissolved in methanol and concentrated to dryness.

XVI. Synthesis of 1-Fluorophenothiazin-5-ium derivatives

Example 1

1-Fluoro-10H-phenothiazine a. Synthesis of N-Acetyl-2-fluoroaniline

Acetic anhydride (57 mL, 0.6 mol) was added slowly, over approximately 40 min., to stirred 2-fluoroaniline (55.7 g, 0.5 mol) under cooling (water bath) to maintain the reaction temperature at 60-70° C. After 10 more hours the reaction mixture was poured into $H_2O$, the whole was extracted with ethyl acetate (2×300 mL). The combined organic extracts were washed with 5% aqueous $NaHCO_3$, brine, dried ($K_2CO_3$), filtered and concentrated to provide the title compound as a white solid (67.0 g, 88%).

b. Synthesis of N-Acetyl-2-fluorodiphenylamine

A mixture of the N-acetyl-2-fluoroaniline (61.2 g, 0.4 mol), anhydrous $K_2CO_3$ (55.2 g, 0.4 mol), CuI (38.0 g, 0.2 mol) and bromobenzene (234 mL, 1.0 mol) was stirred and heated at 175-180° C. under an Argon atmosphere for 72 h. After cooling the reaction mixture was poured into ice-$H_2O$ and extracted with ethyl acetate (2×200 mL), the combined organic extracts were washed with brine, dried over anhydrous $K_2CO_3$, filtered and concentrated to dryness. The obtained crude material was purified by flash chromatography (using ethyl acetate-hexane) to afford the N-acetyl-2-fluorodiphenylamine (74.0 g, 81%).

c. Synthesis of 2-Fluorodiphenylamine

A solution of the N-acetyl-2-fluorodiphenylamine (57.2 g, 0.25 mol) in solution KOH (42 g, 075 mol)/EtOH (250 mL) was stirred and heated at 60° C. for 1 h. Reaction progress was monitored by TLC. Solution was poured into $H_2O$. The mixture was extracted with ethyl acetate (2×100 mL). The combined organic layers were washed with brine, dried ($Na_2SO_4$), filtered and concentrated to dryness, gave title compound (46.8 g, 96%).

d. Synthesis of 1-Fluoro-10H-phenothiazine

To a 2-fluorodiphenylamine (5) (3.66 g, 20 mmol), sulfur (1.22 g, 40 mmol) and iodine (1.52 g, 6 mmol) were added. Vial was charged with balloon for discharge. The hot block was preheated (150° C.). The vial was heated on the hot block and after 15 min. temperature was increased to 210° C., reaction mixture was stirred and heated for an additional 45 min. and cooled. The product was extracted by hexane and purified by flash chromatography (ethyl acetate-hexane) to afford the desired product (2.6 g, 60%).

Example 2

Synthesis of 3,7-Bis-morpholino-1-fluorophenothiazin-5-ium chloride a. Synthesis of 3,7-Dibromo-1-fluoro-10H-phenothiazine 1-Fluoro-10H-phenothiazine (1.34 g, 6.2 mmol) was dissolved in acetic acid (10 mL) and stirred at room temperature as a solution of bromine (2.96 g, 0.95 mL, 18.5 mmol) in acetic acid (50 mL) was added. The mixture was allowed to stir overnight at this condition. To this mixture sodium sulfite $Na_2SO_3$ (1.56 g, 12.4 mmol) and water (2 mL) were added. The mixture was stirred at room temperature for 3 h. After that reaction mixture was poured into 100 mL of ice-water contained NaOH (1.0 g, 25 mmol). The mixture was stirred overnight and filtered, gave light green solid (1.70 g, 73%).

b. Synthesis of 3,7-Dibromo-1-fluoro-10-Boc-phenothiazine 3,7-Dibromo-1-fluoro-10H-phenothiazine (1.7 g, 4.5 mmol) was suspended in $CH_3CN$ (20 mL) and $(Boc)_2O$ (2.94 g, 13.5 mmol) and DMAP (0.55 g, 4.5 mmol) were added. The mixture was warmed to 50 C. After 5 min. starting material was dissolved in solvent, $CO_2$ was eliminated and solid material formed. After 2 h the reaction mixture was cooled to room temperature. The solid was filtered off and dried in air (1.71 g, 80%).

c. Synthesis of 3,7-Bis-morpholino-1-fluoro-10-Boc-phenothiazine

To a stirred solution of 3,7-dibromo-1-fluoro-10-Boc-phenothiazine (8) (238 mg, 0.5 mmol) in touene (10 mL) $Pd(dba)_2$ (14.4 mg, 0.025 mmol), BINAP (10.9 mg, 0.018 mmol), $Cs_2CO_3$ (815 mg, 2.5 mmol) and morpholine (218 mg, 2.5 mmol) were added. The mixture was refluxed for 24 h. After that reaction mixture was filtered, solvent was removed under vacuum. Product was used without additional purification.

d. Synthesis of 3,7-Bis-morpholino-1-fluorophenothiazin-5-ium chloride

To a solution 3,7-bis-morpholino-1-fluoro-10-Boc-phenothiazine (122 mg) in dichloromethane (10 mL) HCl (2 mL, 4 M solution in 1,4-dioxane)) was added. The reaction mixture was stirred at 50° C. for 3 h. Solvent was removed under vacuum. Product was purified by flash chromatography and prep-chromatography.

Example 3

Synthesis of 3-Morpholino-7-(pyrrolidin-1-yl)-1-fluorophenothiazin-5-ium chloride a. Synthesis of 3-Morpholino-1-fluoro-7-bromo-10-Boc-phenothiazine To a stirred solution of 3,7-dibromo-1-fluoro-10-Boc-phenothiazine (8) (290 mg, 0.6 mmol) in toluene (10 mL) $Pd(dba)_2$ (17.3 mg, 0.03 mmol), BINAP (13.5 mg, 0.02 mmol), $Cs_2CO_3$ (390 mg, 1.2 mmol) and morpholine (70 mg, 0.8 mmol) were added. The mixture was refluxed for 24 h. After that reaction mixture was filtered, solvent was removed under vacuum. Product was used without additional purification.

b. Synthesis of 3-Morpholino-7-(pyrrolidin-1-yl)-1-fluoro-10-Boc-phenothiazine

To a stirred solution of 3-morpholino-1-fluoro-7-bromo-10-Boc-phenothiazine (150 mg, 0.3 mmol) in touene (10 mL) $Pd(dba)_2$ (5.8 mg, 0.01 mmol), BINAP (6.3 mg, 0.01 mmol), $Cs_2CO_3$ (326 mg, 1.0 mmol) and pyrrolidine (42.6 mg, 0.6 mmol) were added. The mixture was refluxed for 24 h. After that reaction mixture was filtered, solvent was removed under vacuum. Product was used without additional purification.

c. Synthesis of 3-Morpholino-7-(pyrrolidin-1-yl)-1-fluorophenothiazin-5-ium chloride To a solution 3-morpholino-7-(pyrrolidin-1-yl)-1-fluoro-10-Boc-phenothiazine (150 mg) in dichloromethane (10 mL) HCl (2 mL, 4 M solution in 1,4-dioxane)) was added. The reaction mixture was stirred at 40° C. for 3 h. Solvent was removed under vacuum. Product was purified by flash chromatography.

Example 4

Synthesis of 3-Dimethylamino-7-morpholino-1-fluorophenothiazin-5-ium chloride a. Synthesis of 3-Dimethylamino-1-fluoro-7-bromo-10-Boc-phenothiazine To a stirred solution of 3,7-dibromo-1-fluoro-10-Boc-phenothiazine (1.43 g, 3.0 mmol) in toluene (60 mL) in 75 mL pressure vessel $Pd(dba)_2$ (86.3 mg, 0.15 mmol), BINAP (67.3 mg, 0.11 mmol), $Cs_2CO_3$ (978 mg, 3.0 mmol) and dimethylamine (1.5 mL, 2 M solution in THF) were added. The mixture was refluxed for 24 h. After that reaction mixture was filtered, solvent was removed under vacuum. Product was used without additional purification.

b. Synthesis of 3-Dimethylamino-7-morpholino-1-fluoro-10-Boc-phenothiazine

To a stirred solution of 3-dimethylamino-1-fluoro-7-bromo-10-Boc-phenothiazine (14) (200 mg, 0.45 mmol) in toluene (10 mL) $Pd(dba)_2$ (14.4 mg, 0.025 mmol), BINAP (10.9 mg, 0.018 mmol), $Cs_2CO_3$ (326 mg, 1.0 mmol) and morpholine (87 mg, 1.0 mmol) were added. The mixture was refluxed for 24 h. After that reaction mixture was filtered, solvent was removed under vacuum. Product was used without additional purification.

c. Synthesis of 3-Dimethylamino-7-morpholino-1-fluorophenothiazin-5-ium chloride To a solution 3-dimethylamino-7-morpholino-1-fluoro-10-Boc-phenothiazine (15) (100 mg) in dichloromethane (10 mL) HCl (1 mL, 4 M solution in 1,4-dioxane)) was added. The reaction mixture was stirred at 40° C. for 3 h. Solvent was removed under vacuum. Product was purified by flash chromatography.

Example 5

Synthesis of 3-(1,4-Diazepan-1-yl)-7-morpholino-1-fluorophenothiazin-5-ium chloride a. Synthesis of 3-(4-Boc-1,4-Diazepan-1-yl)-1-fluoro-7-bromo-10-Boc-phenothiazine To a stirred solution of 3,7-dibromo-1-fluoro-10-Boc-phenothiazine (950 mg, 2.0 mmol) in toluene (30 mL) $Pd_2(dba)_3$ (46 mg, 0.05 mmol), BINAP (31 mg, 0.05 mmol), $Cs_2CO_3$ (652 mg, 2.0 mmol) and N-Boc-homopiperazine (1-Boc-1,4-diazepane) (400 mg, 2.0 mmol) were added. The mixture was refluxed for 24 h. After that reaction mixture was filtered, solvent was removed under vacuum. Product was used without additional purification.

b. Synthesis of 3-(4-Boc-1,4-diazepan-1-yl)-7-morpholino-1-fluoro-10-Boc-phenothiazine To a stirred solution of 3-(4-Boc-1,4-diazepan-1-yl)-1-fluoro-7-bromo-10-Boc-phenothiazine (1.1 g, 2.0 mmol) in toluene (10 mL) $Pd_2(dba)_3$ (46 mg, 0.05 mmol), BINAP (31 mg, 0.018 mmol), $Cs_2CO_3$ (652 mg, 2.0 mmol) and morpholine (348 mg, 4.0 mmol) were added. The mixture was refluxed for 24 h. After that reaction mixture was filtered, solvent was removed under vacuum. Product was used without additional purification.

c. Synthesis of 3-(1,4-Diazepan-1-yl)-7-morpholino-1-fluorophenothiazin-5-ium chloride To a solution 3-(4-Boc-1,4-diazepan-1-yl)-7-morpholino-1-fluoro-10-Boc-phenothiazine (0.8 g) in dichloromethane (10 mL) HCl (2 mL, 4 M solution in 1,4-dioxane)) was added. The reaction mixture was stirred at 40° C. for 3 h. Solvent was removed under vacuum. Product was purified by flash chromatography.

Example 6

Synthesis of 7-(1,4-Diazepan-1-yl)-3-morpholino-1-fluorophenothiazin-5-ium chloride The synthesis of the title compound was performed as described for the similar derivatives shown above.

XVII. 1,9-Difluorophenothiazin-5-ium derivatives

Example

1,9-Difluoro-10H-phenothiazine

The synthesis of the title compound was performed as described for the similar derivatives shown above.

Example

Synthesis of 3,7-Bis-morpholino-1,9-difluorophenothiazin-5-ium chloride

The synthesis of the title compound was performed as described for the similar derivatives shown above.

4.6.2 Biological Activity of Compounds

4.6.2.1 Respiratory Viruses

The activities of compounds of the invention were determined for the following viruses using the protocol below:
- Corona Virus on MRC5 Cells
- Influenza Virus A on MDCK Cells
- Respiratory Syncytial Virus on HEp2 cells
- Adenovirus serotype 5 on A549 cells
- Human Rhinovirus on H1Hela Cells
- Herpes Simplex Virus 1 on Vero cells Virus was grown in the presence of four dilutions (10 μM, 2 μM, 0.4 μM and 0.08 μM) of the chemical compound tested with two controls using standard methods and materials for the relevant virus. The infected cell extract was collected using known methods, and the infectious virus concentration was determined using standard techniques.

Each well was titrated by $TCID_{50}$. Four serial dilutions in quadruplicate required to determine the titer of each well. To assay 36 replicates as directed, one hundred eight (108) 96-well plates is required. Each drug was tested at four dilutions against one virus will require $TCID_{50}$ titers of 18 sample wells.

4.6.2.2 Monkey Pox Virus

Compounds of the invention were tested for activity against monkey pox virus using the following protocol:
1. Infected cells with target dose of 100 PFU/well MPXV.
2. One hour later, removed the virus solution and wash cells with media and aspirated.
3. Added serial half-log dilutions of compounds in methyl cellulose to triplicate wells; methyl cellulose is semi-solid media which contains virus in one location, so only the adjacent cells are infected. Each plate included a positive control of virus only wells (triplicate), with methyl cellulose overlay.
4. Four days later, removed the media from wells and added crystal violet to stain the cells.
5. After 20 min to 30 min later, washed the cells with $ddH_2O$ and dried.
6. Counted the plaques.
7. Compared plaque numbers of compound wells with the plaque numbers in virus only wells and determined the difference (percentage) of inhibition vs. protection.

4.6.2.3 Marburg Virus

Compounds of the invention were tested against Marburg virus using the following protocol:

Dimethylsulfoxide (DMSO) in 5 mM concentration was used as a solvent for the compounds and as a control. The compounds tested were stored under argon. Each compound was provided in a vial. The experiments were performed on 24-well plate.

Incubation of Compounds with Cells.

Day 0: Plated Vero cells at $1 \times 10^5$ cells/well in a 1 mL volume of medium (24-well plate), and incubated overnight.

Day 1:
1. Following sterile procedure, diluted each of the four compound stocks in DMSO to concentrations 100-fold greater than will be used in the treatment wells.
2. Further diluted the DMSO stocks 1:100 in EMEM with 10% FBS/Pen/Strep to generate treatments containing 1% DMSO. To generate DMSO control media, diluted DMSO (no compound) to 1% in EMEM with 10% FBS/Pen/Strep.
3. Aspirated the media in cell plates and added 1 mL of compound or control to the appropriate wells.
4. Incubated plate overnight.

Day 2:
1. Dilute virus: Diluted MARV to a concentration of $1 \times 10^6$ pfu/mL EMEM with 10% FBS/Pen/Strep.
2. Infection: Removed media from wells and applied 100 µL diluted virus to each well, except mock-infected well. Applied 100 µL EMEM with 10% FBS to the mock-infected well. Incubated the plate for 1 h at 37° C., rocking the plate gently every 15 min to prevent the cell monolayer from drying out.
3. Wash cells and add compound: After the one-hour infection period, aspirated the virus from the wells and add 1 mL PBS to each well. Aspirated the PBS and immediately added 1 mL diluted compound to the appropriate wells. The DMSO control and mock-infected wells received 1 mL of the DMSO control media.
4. Critical Treatments:
    (a) Compound Treatment Wells
    (b) DMSO control media+virus
    (c) DMSO control media no virus (Mock)
5. Incubated the plates at 37° C. under 5% $CO_2$ for 72 h.

Day 3: Removed as much media as possible from each well and stored at −80° C.

Determination of Plaques.

Day 0: Seeded 6-well plates with $2.5 \times 10^5$ Vero cells/well in 2 mL volumes of medium. Incubated overnight.

Day 1:
1. In deep-well 96-well plates prepared six 1:10 serial dilutions of supernatants from each well beginning with 1:10 and ending with 1:6 in 500 µL volumes EMEM with 2% FBS:
    (a) Diluted 60 µL undiluted supe into 540 µL EMEM with 2% FBS=1:1.
    (b) Diluted 60 µL of the 1:1 supe into 540 µL EMEM with 2% FBS=1:2.
    (c) Diluted 60 µL of the 1:2 supe into 540 µL EMEM with 2% FBS=1:3.
    (d) Diluted 60 µL of the 1:3 supe into 540 µL EMEM with 2% FBS=1:4
    (e) Diluted 60 μL of the 1:4 supe into 540 μL EMEM with 2% FBS=1:5
   (f) Diluted 60 μL of the 1:5 supe into 540 μL EMEM with 2% FBS=1:6
2. Prepared 2% agarose and place in a 37° C. water bath to prevent the solution from solidifying. Prewarm 2×EMEM in a 37° C. water bath.
   (a) Volume of agarose needed=12 mL per undiluted supe sample+extra.
   (b) Volume of 2×EMEM needed is the same.
3. Removed culture supernatant from plated cells and add 200 μL of diluted culture supernantant in duplicate to appropriate wells, according to plate diagram.
4. Incubated each plate for 1 h at 37° C. under 5% $CO_2$, rocking the plate gently every 15 minute.
5. After plates had incubated for 1 h, combined the 2% agarose with the 2×EMEM and mixed well. Gently applied 2 mL overlay to each well without removing the inoculum and swirled the plate gently to mix the inoculum in with the overlay. Repeated this process to apply overlays to each plate.
6. Allowed the overlays to solidify at room temperature for 1 h.

7. Incubated the plates for 5 d at 37° C. under 5% $CO_2$.
8. Stained the cells using a secondary overlay containing neutral red and incubate for 24 h.
9. Quantified the plaques in each well.

Compounds having useful activities in this assay (i.e., an $IC_{50}\leq30$ μmol) include: 3-(dimethylamino)-1,9-dimethyl-7-morpholino-phenothiazin-5-ium-4-carboxylic acid; 1,9-dimethyl-3,7-dimorpholino-phenothiazin-5-ium-4-carboxylic acid; and 4-[7-(dimethylamino)-1,9-dimethyl-phenothiazin-5-ium-3-yl]morpholine-2-carboxylic acid.

4.6.2.4 Influenza Virus

Compounds of the invention were tested for activity against Influenza virus using the following protocol:

1. MDCK (Madin-Darby canine kidney) cells were plated in three 96-well plates ($6\times10^4$ per well) and cultured overnight. The next day the cells were inspected with a microscope to document the confluence. The required amount of wells were infected with the fowl plaque virus (Influenza A/H7N7/Bratislava/1979) with an MOI of 1 (assuming duplication of cells over night to generate $1.2\times10^5$ PFU/well). Infection was performed with 200 μL of virus suspension. All three plates were treated identically and served as triplicates. On each plate was one well with one concentration of substance, three wells with the highest concentration of DMSO that is used on the plate, and three wells with the lowest concentration of DMSO that is on the plate. In addition there were three infected wells that were cultured with cell culture medium without additional substance. There also were 12 wells on every plate that were not infected and served as controls for the cpe determination and for the neutral red staining.
2. Substances were diluted before cells were infected and plates in 96-well plates so that they could easily be plated on the infected cells.
3. Infection was performed for 30 min at 37° C. in a cell culture incubator.
4. After infection the cells were washed once with infection-PBS. During washing the cell monolayer was inspected with a microscope, and damaged monolayers were excluded from testing. Uninfected wells were mock infected with infection-PBS and also inspected visually.
5. The pattern of substances on every individual plate was marked on the top of the plate and on a scheme.
6. An aliquote of 250 μL of diluted substance was used and cells were incubated for 16 h. After incubation time the cell monolayer was again inspected and cpe was monitored and recorded.
7. Supernatants of the first plate were transferred to a 96-well ELISA-plate and kept cool for titration, which was performed later the same day.
8. Cells of this plate were washed carefully with PBS again inspected at the microscope and then stained with neutral red (which is staining the living cells) for 3 hours at 37° C. (neutral red is used at the concentration 1 mg/20 mL MEM; 200 μL/well.
9. In the meantime the dilutions for the titration were generated in a 96-well plate by diluting the supernatants 1:10. A 100 μL aliquot of undiluted supernatant and five dilutions (from $10^{-1}$ to $10^{-5}$ were used to infect 24-wells of MDCK monolayers of cells. This means that at this time point we only titrate one unique copy of every tested substance. The other three plates were immediately frozen at −70° C. and stored until titration.

10. The neutral red staining was stopped by washing the monolayer three times very carefully with PBS and the plate was dried on cellulose to eliminate residual PBS.
11. The neutral red was dissolved from the cells by using Ethanol/acidic acid for 15 min on a plate rocking platform.
12. The Ethanol/acidic acid was transferred to an Elisaplate and measured at 570 nm in an Elisa-reader.
13. The percentage of live cells was calculated setting the non-infected cells to 100%.

Compounds having useful activities against influenza as determined by this assay, viz. compounds having values of $IC_{50} \leq 30$ μmol, include but are not limited to: 4-(9-ethyl-1-methyl-7-piperazin-1-yl-phenothiazin-5-ium-3-yl)morpholine; 3-(dimethylamino)-1,9-dimethyl-7-morpholino-phenothiazin-5-ium-4-carboxylic acid; 1,9-dimethyl-3,7-dimorpholino-phenothiazin-5-ium-4-carboxylic acid; 4-[7-(dimethylamino)-1,9-dimethyl-phenothiazin-5-ium-3-yl] morpholine-2-carboxylic acid; 4-[7-(2,6-dimethylmorpholin-4-yl)-1-ethyl-9-methyl-phenothiazin-5-ium-3-yl]-2,6-dimethyl-morpholine; 1-(9-ethyl-1-methyl-7-morpholino-phenothiazin-5-ium-3-yl)-N,N-dimethyl-piperidin-4-amine; 4-(1,9-diethyl-7-morpholino-phenothiazin-5-ium-3-yl)piperazine-1-sulfonamide; 4-[7-(azetidin-1-yl)-1,9-dimethyl-phenothiazin-5-ium-3-yl] morpholine; 4-(1-methyl-7-morpholino-phenothiazin-5-ium-3-yl)morpholine; 1-(1,9-diethyl-7-morpholino-phenothiazin-5-ium-3-yl)piperidine-3-carboxamide; 4-[7-(azetidin-1-yl)-1,9-diethyl-phenothiazin-5-ium-3-yl] morpholine; 4-(1,9-diethyl-7-morpholino-phenothiazin-5-ium-3-yl)-1,4-thiazinane 1,1-dioxide; 4-(1,9-dimethyl-7-morpholino-phenothiazin-5-ium-3-yl)piperazine-1-sulfonamide; (2R,6S)-4-[7-[(2R,6S)-2,6-dimethylmorpholin-4-yl]-1,9-dimethylphenothiazin-5-ium-3-yl]-2,6-dimethylmorpholine; (2R,6S)-4-[7-[(2R,6R)-2,6-dimethylmorpholin-4-yl]-1,9-dimethyl-phenothiazin-5-ium-3-yl]-2,6-dimethyl-morpholine; (2R,6S)-4-(1,9-dimethyl-7-morpholino-phenothiazin-5-ium-3-yl)-2,6-dimethyl-morpholine; (2S,6S)-4-(1,9-dimethyl-7-morpholino-phenothiazin-5-ium-3-yl)-2,6-dimethyl-morpholine; 4-(1,9-dimethyl-7-piperazin-1-yl-phenothiazin-5-ium-3-yl)morpholine; 4-(1-ethyl-7-morpholinophenothiazin-5-ium-3-yl)morpholine; tert-butyl 4-(1-ethyl-9-methyl-7-morpholino-phenothiazin-5-ium-3-yl)-1,4-diazepane-1-carboxylate; 4-[7-(1,4-diazepan-1-yl)-9-ethyl-1-methyl-phenothiazin-5-ium-3-yl]morpholine; yl)morpholine; tert-butyl 4-(7-morpholino-1-sec-butyphenothiazin-5-ium-3-yl)-1,4-diazepane-1-carboxylate; 4-[7-(1,4-diazepan-1-yl)-9-sec-butyl-phenothiazin-5-ium-3-yl]morpholine; 4-(1-isopropyl-7-morpholino-phenothiazin-5-ium-3-yl)morpholine; 4-(1-tert-butyl-7-morpholino-phenothiazin-5-ium-3-yl)morpholine; N-tert-butyl-4-(7-morpholino-1-sec-butyphenothiazin-5-ium-3-yl)-1,4-diazepane-1-carboxamide; tert-butyl 4-(1-isopropyl)-morpholino-phenothiazin-5-ium-3-yl)-1,4-diazepane-1-carboxylate; 4-[7-(1,4-diazepan-1-yl9-isopropyl-phenothiazin-5-ium-3-yl]morpholine; 4-(1-fluoro-7-pyrrolidin-1-yl-phenothiazin-5-ium3-yl)morpholine; 4-[7-(4,4-difluoro-1-piperidyl)-1,9-dimethyl-phenothiazin-5-ium-3-yl]morpholine-4-[7-(azepan-1-yl)-9-isopropyl-phenothiazin-5-ium-3-yl]morpholine; 4-[7-(4-isopropylsulfonyl-1,4-diazepan-1-yl)-9-sec-butyl-phenothiazin-5-ium-3-yl]morpholine; and 4-[7-(4-cyclopropylsulfonyl-1,4-diazepan-1-yl)-9-sec-butyl-phenothiazin-5-ium-3-yl]morpholine.

4.6.2.5 Ebola Virus

Compounds of the invention were tested for activity against Ebola virus using the following protocol:

Concentration of Compound: 10 mM DMSO stock. Day 0: Vero cells were plated at $1 \times 10^5$ cells/well in a 1 mL volume of medium (24-well plate), and incubate overnight.

Day 1: Compound Dilutions
1. Following sterile procedure, diluted each of the four compound stocks in DMSO to concentrations 100-fold greater than will be used in the treatment wells.
2. Further diluted the DMSO stocks 1:100 in EMEM with 10% FBS/Pen/Strep to generate treatments containing 1% DMSO. To generate DMSO control media, diluted DMSO (no compound) to 1% in EMEM with 10% FBS/Pen/Strep.
3. Aspirated the media in cell plates and add 1 mL of compound or control to the appropriate wells.
4. Incubated plate overnight.

Day 2:
1. Diluted virus: Diluted EBOV to a concentration of $1 \times 10^6$ PFU/mL Eagle's Minimum Essential Medium (EMEM) with 10% FBS/Pen/Strep.
2. Infection: Removed media from wells and applied 100 μL diluted virus to each well, except mock-infected well. Applied 100 μL) EMEM with 10% FBS to the mock-infected well. Incubated the plate 1 h at 37° C., rocking the plate gently every 15 min to prevent the cell monolayer from drying out.
3. Washed cells and added compound. After the 1 h infection period, aspirated the virus from the wells and added 1 mL PBS to each well. Aspirated the PBS and immediately added 1 mL diluted compound to the appropriate wells. The DMSO control and mock-infected wells received 1 mL of the DMSO control media.
4. Critical Treatments:
   (a) Compound Treatment Wells
   (b) DMSO control media+virus
   (c) DMSO control media no virus (Mock)
5. Incubated the plates: Incubated the plates at 37° C. under 5% $CO_2$ for 72 h.

Day 3:
Removed the supernatant from infected plates: Removed as much media as possible from each well and stored at −80° C.

Plaque Assay:
Day 0:
1. Seeded 6-well plates with $2.5 \times 10^5$ Vero cells/well in 2 mL volumes of medium. Incubated overnight.

Day 1:
1. In deep-well 96-well plates prepared six 1:10 serial dilutions of supernatants from each well beginning with 1:10 and ending with $1:10^6$ in 500 μL volumes of EMEM with 2% FBS:
   (a) Diluted 60 μL undiluted supe into 540 μL EMEM with 2% FBS=$1:10^1$.
   (b) Diluted 60 μL of the $1:10^1$ supe into 540 μL EMEM with 2% FBS=$1:10^2$.
   (c) Diluted 60 μL of the $1:10^2$ supe into 540 μL EMEM with 2% FBS=$1:10^3$.
   (d) Diluted 60 μL of the $1:10^3$ supe into 540 μL EMEM with 2% FBS=$1:10^4$
   (e) Diluted 60 μL of the $1:10^4$ supe into 540 μL EMEM with 2% FBS=$1:10^5$
   (f) Diluted 60 μL of the $1:10^5$ supe into 540 μL EMEM with 2% FBS=$1:10^6$
2. Prepared 2% agarose and placed in a 37° C. water bath to prevent the solution from solidifying. Prewarmed 2×EMEM in a 37° C. water bath.
   (a) Volume of agarose needed=12 mL per undiluted supe sample+extra.
   (b) Volume of 2×EMEM needed is the same.
3. Removed culture supernatant from plated cells and added 200 μL of diluted culture supernatant in duplicate to appropriate wells, according to plate diagram.

4. Incubated each plate for 1 h at 37° C. under 5% $CO_2$, rocking the plate gently every 15 min.
5. After plates had incubated for 1 h, combined the 2% agarose with the 2×EMEM and mixed well. Gently applied 2 mL overlay to each well without removing the inoculum and swirled the plate gently to mix the inoculum in with the overlay. Repeated this process to apply overlays to each plate.
6. Allowed the overlays to solidify at room temperature for 1 h.
7. Incubated the plates for 5 d at 37° C. under 5% $CO_2$.
8. Stained the cells using a secondary overlay containing neutral red and incubated for 24 h.
9. Quantified the plaques in each well.

Compounds having useful activities against ebola virus as determined by this assay, viz. compounds having values of $IC_{50}$≤30 μmol, include but are not limited to: 4-(9-ethyl-1-methyl-7-morpholino-phenothiazin-5-ium-3-yl)-1,4-thiazinane 1,1-dioxide.

4.6.2.6 Dengue, Easter Equine Encephalitis, Venezuelan Equine Encephalitis, Western Equine Encephalitis, West Nile, and Chikungunya Viruses Compounds of the invention were tested for activity against Dengue, Easter Equine Encephalitis, Venezuelan Equine Encephalitis, Western Equine Encephalitis, West Nile, and Chikungunya Viruses using the following protocol:

1. The Set test sample was set up in ten-fold dilutions across a 96-well plate. A mixture of 270 μL HBSS with HEPES and 2% FBS with Pen/Strep or complete media 2% FBS was added to each well. To the first well in each row 30 μL of test sample was introduced (i.e., a 1:10 dilution) and mixed. A 30 μL aliquot was transferred from the first well to next well, and so on. Dilutions out to well #9 were made to provide a range of dilutions from $10^{-1}$ to $10^{-9}$. Be sure to discard tips between transfers.
2. Once dilutions were ready the plates were labeled with sample number and dilutions (plates can be labeled at any time prior to infection). Each dilution was plated on two wells. If plating dilutions $10^{-1}$ to $10^{-9}$, requires three plates per sample.
3. The media was removed from six-well plates by inverting over a dispo pan containing microchem disinfectant. Then 100 μL was added to each well of virus dilution. A duplicate was done to obtain an average. The plates were incubated at 37° C., 5% $CO_2$ for 1 h with occasional rocking (approximately every 15 min).
4. Preparation of media and agarose for overlay. Final concentration 1×EMEM, 10% FBS, 1% Pen/Strep, 0.1% gentamycin, in a 0.6% agarose solution (see cell culture overlay without neutral red chart). Added about 2 mL of overlay to each well and returned to the incubator. (It is not necessary to allow to solidify prior to placing in the incubator.) Incubated overnight at 37° C., 5% $CO_2$.
5. Next day: The resulting plaques were visualized with Neutral Red. A media/agarose overlay was prepared as above with 4% neutral red solution added to the media/agarose overlay as prepared in Step 4 (see cell culture overlay with neutral red overlay chart). Added about 2 mL ml per well.
6. Incubated the plates overnight at 37° C., 5% $CO_2$.
7. Counted plaques.

Compounds having useful activities against one or more of the above-described viruses as determined by these assays, viz. compounds having values of $IC_{50}$≤30 μmol, include but are not limited to: 4-(9-ethyl-1-methyl-7-piperazin-1-yl-phenothiazin-5-ium-3-yl)morpholine; 3-(dimethylamino)-1,9-dimethyl-7-morpholino-phenothiazin-5-ium-4-carboxylic acid; 1,9-dimethyl-3,7-dimorpholino-phenothiazin-5-ium-4-carboxylic acid; 4-(9-ethyl-1-methyl-7-morpholino-phenothiazin-5-ium-3-yl)-1,4-thiazinane-1,1-dioxide; 4-(1,9-diethyl-7-morpholino-phenothiazin-5-ium-3-yl)piperazine-1-sulfonamide; 4-(1-methyl-7-morpholino-phenothiazin-5-ium-3-yl)morpholine; 1-(1,9-diethyl-7-morpholino-phenothiazin-5-ium-3-yl)piperidine-3-carboxamide; 4-(1,9-diethyl-7-morpholino-phenothiazin-5-ium-3-yl)-1,4-thiazinane-1,1-dioxide; and N-[1-(1,9-diethyl-7-morpholino-phenothiazin-5-ium-3-yl)-4-piperidyl] cyclopropane sulfonamide.

4.6.2.7 HIV Virus

H9 cells were obtained from the AIDS Research and Reference Reagent Program. A chronically infected cell population was generated by infection with HIV-1 SK-1 (references 1 & 2 below) and long term culture. Cells were maintained under standard culture conditions in RPMI 1640 supplemented with 15% fetal bovine serum (heat inactivated), 2 mM L-glutamate, 100 U $mL^{-1}$ penicillin and 100 μg $mL^{-1}$ streptomycin. Cultures are maintained in such a way as to ensure exponential growth of the populations. At the time of the assay cells are collected by centrifugation and counted by hemacytometer. If cell viability by Trypan Blue dye exclusion is less than 90% the assay is terminated. The cells are adjusted to $3\times10^5$ cells $mL^{-1}$ and 100 μL placed in 96-well plates with 100 μL media containing the test compound. Cultures are incubated for 3 d and supernatants harvested. Compound toxicity is determined by MTS dye reduction. Virus expression is measured by supernatant reverse transcriptase activity and subsequent determination of supernatant virus infectivity by MAGI assay.

Reverse Transcriptase Activity Assay

A microtiter plate-based reverse transcriptase (RT) reaction was utilized (Buckheit et al., *AIDS Research and Human Retroviruses* 7:295-302, 1991). Tritiated thymidine triphosphate ($^3$H-TTP, 80 Ci $mmol^{-1}$, NEN) was received in 1:1 $dH_2O$:Ethanol at 1 mCi $mL^{-1}$. Poly rA:oligo dT template: primer (Pharmacia) was prepared as a stock solution by combining 150 μLpoly rA (20 mg $mL^{-1}$ with 0.5 mL oligo dT (20 U $mL^{-1}$) and 5.35 mL sterile $dH_2O$ followed by aliquoting (1.0 mL) and storage at −20° C. The RT reaction buffer was prepared fresh on a daily basis and consists of 125 μL 1.0 M EGTA, 125 μL $dH_2O$, 125 μL 20% Triton X100, 50 μL 1.0 M Tris (pH 7.4), 50 μL 1.0 M DTT, and 40 μL 1.0 M $MgCl_2$. The final reaction mixture was prepared by combining 1 part $^3$H-TTP, 4 parts $dH_2O$, 2.5 parts poly rA:oligo dT stock and 2.5 parts reaction buffer. Ten microliters of this reaction mixture was placed in a round bottom microtiter plate and 15 μL of virus containing supernatant was added and mixed. The plate was incubated at 37° C. for 60 min. Following incubation, the reaction volume was spotted onto DE81 filter-mats (Wallac), washed 5 times for 5 min each in a 5% sodium phosphate buffer or 2×SSC (Life Technologies). Next they were washed 2 times for 1 min each in distilled water, 2 times for 1 min each in 70% ethanol, and then dried. Incorporated radioactivity (counts per minute, CPM) was quantified using standard liquid scintillation techniques.

MTS Staining for Cell Viability

At assay termination, assay plates were stained with the soluble tetrazoliumbased dye MTS 3-(4,5-dimethylthiazol-2-yl)-5-(3-carboxymethoxyphenyl)-2-(4-sulfophenyl)-2H- tetrazolium; CellTiter 96 Reagent, Promega) to determine cell viability and quantify compound toxicity. The mitochondrial enzymes of metabolically active cells metabolize MTS to yield a soluble formazan product. This allows the rapid quantitative analysis of cell viability and compound cytotoxicity. The MTS is a stable solution that does not require preparation before use. At termination of the assay, 20 μL of MTS reagent was added per well. The microtiter plates were then incubated 4 h to 6 h at 37° C. The incubation intervals were chosen based on empirically determined times for optimal dye reduction. Adhesive plate sealers were used in place of the lids, the sealed plate was inverted several times to mix the soluble formazan product and the plate was read spectrophotometrically at 490/650 nm with a Molecular Devices SPECTRAMAXPLUS plate reader.

Determination of Virus Infectivity Using MAGI Cells

This assay uses MAGI cells (HeLa—CD4-LTR-β-gal cells; AIDS Research and Reference Reagent Repository, Bethesda, Md.), that contain one copy of the HIV-1 LTR promoter that drives expression of the β-galactosidase gene upon HIV-1 Tat transactivation. Thus, the expression of β-galactosidase was measured as a function of virus infection of the cells. Twenty-four hours prior to initiation of the assay, MAGI cells were plated in 96 flatwell plates. On the day of the assay, media was removed from the wells and 50 μL of supernatant was transferred from the ACH-2 or H9/SK-1 cultures onto the MAGI cells. The plates were incubated for 1 h at 37° C. Fresh media (150 μL was then added to the wells for a final volume of 200'L. Plates were incubated for 7 d. A chemiluminescent endpoint was used to determine the extent of β-galactosidase expression as a measure of HIV-1 infection of the cells. At 7 d post infection, plates were aspirated and PBS was added to each well. Subsequently, detection of β-galactosidase activity was determined by measurement of relative chemiluminescence per manufacturer's instructions (TROPIX GAL-screen, Applied Biosystems, Bedford, Mass.).

Data Analysis

The $IC_{50}$ (50%, inhibition of virus replication) was calculated, $TC_{50}$ (50% reduction in cell viability), and a therapeutic index ($TI=IC_{50}/IC_{50}$) were determined.

Compounds having useful activities against influenza as determined by this assay, viz. compounds having values of $IC_{50} \leq 30$ μmol, include but are not limited to: 7-[bis(2-methoxyethyl)amino]-3H-phenothiazin-3-one, 7-(pyrrolidin-1-yl)-3H-phenothiazin-3-one, 1,9-dimethyl-7-(4-methylpiperazin-1-yl)-3H-phenothiazin-3-one, 7-[bis(2-methoxyethyl)amino]-1,9-dimethyl-3H-phenothiazin-3-one, 7-(dimethylamino)-3H-phenothiazin-3-one, 1,9-dimethyl-7-(morpholin-4-yl)-3H-phenothiazin-3-one, 1,9-dimethoxy-7-(pyrrolidin-1-yl)-3H-phenothiazin-3-one, 7-(dimethylamino)-1,9-dimethyl-3H-phenothiazin-3-one, 1,9-dichloro-7-(pyrrolidin-1-yl)-3H-phenothiazin-3-one, and 7-(azetidin-1-yl)-3H-phenothiazin-3-one.

REFERENCES

The following references are incorporated in there entireties and for all purposes.
1. Cloyd, M. W., and B. E. Moore. 1990. Spectrum of biological properties of human immunodeficiency virus (HIV-1) isolates. *Virology* 174:103-116.
2. C. Lackman-Smith, et al. 2008. Development of a Comprehensive Human Immunodeficiency Virus Type 1 Screening Algorithm for Discovery and Preclinical Testing of Topical Microbicides. *Antimicrobial Agents & Chemotherapy* 52(5):1768-1781.

HCV Live Virus Assay

HCV infection in cell culture was performed using Huh7 hepatoma cells transduced with a lentiviral vector containing a Gaussia luciferase reporter (G-Luc) gene as reported previously (see below); the luciferase reporter is secreted into the media and provides a convenient measure of cell number and viability. Measurement of virus replication (RNA replication, assembly, release, and infection) was enhanced by including a firefly luciferase reporter gene into the context of the Jc1 chimera. Since the firefly luciferase and the gaussia-luciferase utilize different substrates (luciferin, and coelenteracine, respectively) and were cell associated or secreted, respectively, both HCV replication and cell viability could be determined in parallel.

Jc1-F-Luc was transfected into Huh7-G-Luc cells and the test compound wasadded after four hours. Forty-eight hours post transfection (44 hours after compound addition), the media was removed and added to nave cells. Another 48 h later the inoculated cells were harvested and both firefly and gaussia luciferase activity was determined. In this assay format, the firefly luciferase activity was proportional to the efficiency of HCV replication in transfected cells, assembly of progeny particles in the transfected cells, the infectivity of the released particles and replication in the infected cells. Therefore, this type of assay interrogates the complete viral life cycle, in principle allowing detection of interference with any phase of the viral replication process. Using cells transfected with subgenomic HCV replicons (lacking the structural proteins) we will specifically assess possible effects of selected compounds on HCV RNA replication and translation. Finally we will employ HCV pseudoparticles (HCVpp); i.e. retroviral or lentiviral cores surrounded by an envelope containing HCV glycoproteins to selectively analyze interference of any of the compounds with HCV entry. In addition to the HCV specific firefly luciferase signals we will assess gaussia luciferase activity to monitor cell number and viability. During the initial screening each individual compound will be analyzed in three different doses. Based on the HCV-specific dose response, compounds will be prioritized for more detailed characterization.

Compounds having useful activities against influenza as determined by this assay, viz. compounds having values of $IC_{50} \leq 30$ μmol, include but are not limited to: 4-(9-ethyl-1-methyl-7-piperazin-1-yl-phenothiazin-5-ium-3-yl)morpholine; 3-(dimethylamino)-1,9-dimethyl-7-morpholino-phenothiazin-5-ium-4-carboxylic acid; 1,9-dimethyl-3,7-dimorpholino-phenothiazin-5-ium-4-carboxylic acid; 4-(9-ethyl-1-methyl-7-morpholino-phenothiazin-5-ium-3-yl)-1,4-thiazinane-1,1-dioxide; 1-(9-ethyl-1-methyl-7-morpholino-phenothiazin-5-ium-3-yl)-N,N-dimethyl-piperidin-4-amine; 4-(1,9-diethyl-7-morpholino-phenothiazin-5-ium-3-yl)piperazine-1-sulfonamide; 4-[7-(azetidin-1-yl)-1,9-dimethyl-phenothiazin-5-ium-3-yl]morpholine; 4-(1,9-dimethyl-7-thiomorpholinophenothiazin-5-ium-3-yl)morpholine; and 4-(1-methyl-7-morpholino-phenothiazin-5-ium-3-yl)morpholine.

The following references are incorporated in there entireties and for all purposes.
1. Wakita, T. et al. "Production of infectious hepatitis C virus in tissue culture from a cloned viral genome." *Nat Med* 11, 791-6 (2005).
2. Zhong, J. et al. "Robust hepatitis C virus infection in vitro." *Proc Natl Acad Sci USA* 102, 9294-9 (2005).
3. Koutsoudakis, G. et al. "Characterization of the early steps of hepatitis C virus infection by using luciferase reporter viruses." *J Virol* 80, 5308-20 (2006).

4. Pietschmann, T. et al. "Construction and characterization of infectious intragenotypic and intergenotypic hepatitis C virus chimeras." *Proc Natl Acad Sci USA* 103, 7408-13 (2006).
5. de Chassey, B. et al. "Hepatitis C virus infection protein network." *Mol Syst Biol* 4, 230 (2008).
6. Bartosch, B., Dubuisson, J. & Cosset, F. "Infectious hepatitis C virus pseudoparticles containing functional E1-E2 envelope protein complexes." *J Exp Med* 197, 633-42 (2003).
7. Hsu, M. et al. "Hepatitis C virus glycoproteins mediate pH-dependent cell entry of pseudotyped retroviral particles." *Proc Natl Acad Sci USA* 100, 7271-6 (2003)

4.6.2.8 Avicel Plaque Procedure for Junin and Related Viruses

1. Preparation.
    In a 96-well plate (or appropriate size tube), make a 1:10 dilution of test samples and virus control and serial dilute from $10^{-1}$ to $10^{-8}$ as follows: (More of fewer dilutions may be prepared, if needed).
2. Plaque Assay (Day 0).
    Add 200 μL of each dilution, in triplicate, to the appropriate wells, starting with the highest dilution ($10^{-8}$, $10^{-7.5}$, $10^{-6}$ and $10^{-6.5}$, etc.). Pipette down the side of the well and (at a minimum) change tips between each triplicate dilution.
    Incubate at 35° C. to 39° C. for 45 min to 60 min, rocking gently approximately every 15 min.
    Prepare the overlay by diluting PN2098 (Avicel Overlay) and PN2099 (2×MEM Complete) 1:1 to obtain a one-fold concentration. Mix well.
    Using a serological pipette, add 2 mL of the overlay to each well. Pipette down the side of the well, starting with the highest dilution ($10^{-8}$, $10^{-7.5}$, $10^{-6}$ and $10^{-6.5}$, etc.).
    Swirl plates gently to mix and incubate at 35° C. to 39° C. for a minimum of 4 d. (Note: Plaques may be incubated for up to 12 d before staining, depending on the type of virus.)
3. Stain Cells and Count Plaques (Day 4-12).
    Gently swirl the plates to loosen the avicel.
    Add 1 mL of 0.4% crystal violet stain (PN3000) directly to each well.
    Mix gently and incubate overnight at room temperature.
    Decant the crystal violet by dunking in H₂O and allow drying.

Compounds having useful activities against influenza as determined by this assay, viz. compounds having values of $IC_{50} \leq 30$ mmol, include but are not limited to: 4-(9-ethyl-1-methyl-7-piperazin-1-yl-phenothiazin-5-ium-3-yl)morpholine; 4-(9-ethyl-1-methyl-7-morpholino-phenothiazin-5-ium-3-yl)-1,4-thiazinane 1,1-dioxide; 4-(1-methyl-7-morpholino-phenothiazin-5-ium-3-yl)morpholine; 1-(1,9-diethyl-7-morpholino-phenothiazin-5-ium-3-yl)piperidine-3-carboxamide; and N-[1-(1,9-diethyl-7-morpholino-phenothiazin-5-ium-3-yl)-4-piperidyl]cyclopropane sulfonamide.

5 CONCLUSION

The above description of the embodiments, alternative embodiments, and specific examples, are given by way of illustration and should not be viewed as limiting. Further, many changes and modifications within the scope of the present embodiments may be made without departing from the spirit thereof, and the present invention includes such changes and modifications.

What is claimed:
1. A compound which has the structure:

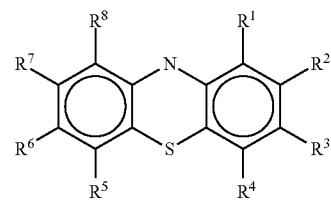

and its pharmaceutically acceptable salts and hydrates, wherein:
   $R^1$ is optionally substituted alkyl,
   $R^8$ is hydrogen or optionally substituted alkyl,
   $R^2$, $R^4$, $R^5$, and $R^7$ are hydrogen;
   $R^6$ is selected from the group consisting of: amino, optionally substituted alkylamino, optionally substituted dialkylamino, and optionally substituted four-, five-, six-, seven-, and eight-membered cycloheteroalkyl, said optionally substituted four-, five-, six-, seven-, and eight-membered cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, optionally substituted sulfinyl, and optionally substituted sulfonyl; and dialkylimino, diarylimino, di-heteroarylimino, alkylarylimino, alkylheteroarylimino, arylheteroarylimino, amino, alkylamino, dialkylamino, alkyloxyalkylamino, di-(alkyloxyalkyl)amino, alkylaminoalkylamino, di-(alkylaminoalkyl)amino, aryloxyalkylamino, di-(aryloxyalkyl)amino, arylaminoalkylamino, di-(arylaminoalkyl)amino, heteroaryloxyalkylamino, di-(heteroaryloxyalkyl)amino, heteroarylaminoalkylamino, and di-(heteroarylaminoalkyl)amino, each of which is optionally substituted; and
   $R^3$ is optionally substituted morpholin-1-yl
wherein said optionally substituted is with a group which is hydrooxyl, nitro, amino, imino, cyano, halo, amidino, oxo, oxamidino, methoxamidino, imidino, guanidino, sulfonamido, carboxyl, formyl, lower alkyl, halolower-alkyl, loweralkoxy, haloloweralkoxy, lower alkoxyalkyl, alkylcarbonyl, arylcarbonyl, aralkylcarbonyl, heteroarylcarbonyl, heteroaralkylcarbonyl, aminoalkyl, or cyanoalkyl
or a compound which has the structure:

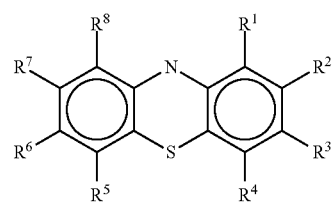

and its pharmaceutically acceptable salts and hydrates, wherein:
   $R^1$ is hydrogen or optionally substituted alkyl,
   $R^8$ is optionally substituted alkyl,
   $R^2$, $R^4$, $R^5$, and $R^7$ are hydrogen;

$R^6$ are selected independently from the group consisting of: amino, optionally substituted alkylamino, optionally substituted dialkylamino, and optionally substituted four-, five-, six-, seven-, and eight-membered cycloheteroalkyl, said optionally substituted four-, five-, six-, seven-, and eight-membered cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, optionally substituted sulfinyl, and optionally substituted sulfonyl; and dialkylimino, diarylimino, di-heteroarylimino, alkylarylimino, alkylheteroarylimino, arylheteroarylimino, amino, alkylamino, dialkylamino, alkyloxyalkylamino, di-(alkyloxyalkyl)amino, alkylaminoalkylamino, di-(alkylaminoalkyl)amino, aryloxyalkylamino, di-(aryloxyalkyl)amino, arylaminoalkylamino, di-(arylaminoalkyl)amino, heteroaryloxyalkylamino, di-(heteroaryloxyalkyl)amino, heteroarylaminoalkylamino, and di-(heteroarylaminoalkyl)amino, each of which is optionally substituted; and $R^3$ is optionally substituted morpholin-1-yl wherein said optionally substituted is with a group which is hydrooxyl, nitro, amino, imino, cyano, halo, amidino, oxo, oxamidino, methoxamidino, imidino, guanidino, sulfonamido, carboxyl, formyl, lower alkyl, haloloweralkyl, loweralkoxy, haloloweralkoxy, lower alkoxyalkyl, alkylcarbonyl, arylcarbonyl, aralkylcarbonyl, heteroarylcarbonyl, heteroaralkylcarbonyl, aminoalkyl, or cyanoalkyl.

2. A compound of claim 1, wherein $R^1$ and $R^8$ are selected independently from optionally substituted methyl or optionally substituted ethyl.

3. A compound of claim 2, wherein $R^6$ is selected from the group consisting of: amino and optionally substituted alkylamino, optionally substituted dialkylamino, optionally substituted alkyloxyalkylamino, and optionally substituted di-(alkyloxyalkyl)amino.

4. A compound of claim 3, wherein $R^6$ is optionally substituted dialkylamino.

5. A compound of claim 4, wherein $R^6$ is optionally substituted di-(alkyloxyalkyl)amino.

6. A compound of claim 1, wherein the compound having the structure:

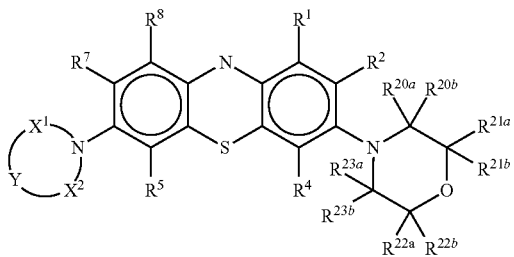

and its pharmaceutically acceptable salts, hydrates, and coordination compounds, wherein Y is $CR^9R^{10}$, $NR^{11}$, O, S, SO, $SO_2$, $SOR^{12}$, and $SO_2R^{13}$, a single bond, or double bond; and $X^1$ and $X^2$ are $(CR^{14}R^{15})_m$ and $(CR^{16}R^{17})_n$ respectively, wherein each of m and n is either 1, 2, or 3 such that the sum m+n is either 2, 3, 4, 5, or 6, and for each of the m and n methylene units of $X^1$ and $X^2$, each of $R^9$-$R^{17}$ is selected independently from the group consisting of: hydrogen, halo, cyano, nitro, amino, carboxyl, formyl, alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, alkyloxycarbonyl, aryloxycarbonyl, heteroaryloxycarbonyl, cycloalkyloxycarbonyl, cycloheteroalkyloxycarbonyl, aralyoxycarbonyloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted; and each of $R^{20a}$-$R^{23b}$ is selected independently from the group consisting of: hydrogen, halo, cyano, nitro, amino, carboxyl, formyl, alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

7. A compound of claim 6, wherein m=n=2.

8. A compound of claim 7, wherein $R^1$ and $R^8$ are selected independently from optionally substituted methyl or and optionally substituted ethyl.

9. A compound of claim 8, wherein Y is O.

10. A compound of claim 8, wherein Y is $NR^{11}$.

11. A compound of claim 8, wherein Y is a single bond.

12. A compound of claim 6, wherein m=3 and n=2.

13. A compound of claim 12, wherein Y is $NR^{11}$.

14. A compound of claim 13, wherein $R^1$ and $R^8$ are independently selected optionally substituted alkyl.

15. A compound of claim 14, wherein $R^1$ and $R^8$ are selected independently from optionally substituted methyl or and optionally substituted ethyl.

16. A method for treating a viral disease in a mammal afflicted with such disease, comprising administering to such mammal a therapeutically effective amount of the compound of claim 1.

17. A compound of claim 1, which is 4-[7-(4,4-difluoro-1-piperidyl)-1,9-dimethylphenothiazin-5-ium-3-yl]morpholine.

18. A method of claim 16, wherein said viral disease is Flu, HCV, HIV, EBOV, MARB, DENV, JUNV, YFV, VEEV, CHIKV, or WNV.

19. A method of claim 16, wherein said viral disease is HIV.

20. A method of claim 16, wherein said viral disease is flu.

21. A compound of claim 1, which is ethyl 4-[7-(dimethylamino)-1,9-dimethyl-phenothiazin-5-ium-3-yl]morpholine-2-carboxylate, 4-[7-(dimethylamino)-1,9-dimethyl-phenothiazin-5-ium-3-yl]morpholine-2-carboxylic acid, 4-[7-(azetidin-1-yl)-1,9-dimethyl-phenothiazin-5-ium-3-yl]morpholine, 4-(1,9-dimethyl-7-thiomorpholino-phenothiazin-5-ium-3-yl)morpholine, (2R,6S)-4-[7-[(2R,6S)-2,6-dimethylmorpholin-4-yl]-1,9-dimethyl-phenothiazin-5-ium-3-yl]-2,6-dimethyl-morpholine, (2R,6S)-4-[7-[(2R,6R)-2,6-dimethyl-morpholin-4-yl]-1,9-dimethyl-phenothiazin-5-ium-3-yl]-2,6-dimethyl-morpholine, (2R,6S)-4-(1,9-dimethyl-7-morpholino-phenothiazin-5-ium-3-yl)-2,6-dimethyl-morpholine, (2S,6S)-4-(1,9-dimethyl-7-morpholino-phenothiazin-5-ium-3-yl)-2,6-dimethyl-morpholine, tert-butyl 4-(1,9-dimethyl-7-morpholino-phenothiazin-5-ium-3-yl)piperazine-1-carboxylate, 4-(1,9-dimethyl-7-piperazin-1-yl-phenothiazin-5-ium-3-yl)morpholine, 4-(1,9-dimethyl-7-piperazin-1-yl-phenothiazin-5-ium-3-yl)morpholine, 4-[1,9-dimethyl-7-(4-methylpiperazin-1-yl)phenothiazin-5-ium-3-yl]morpholine, 4-[7-[(4aR,8aS)-3,4,4a,5,6,7,8,8a-octahydro-2H-quinolin-1-yl]-1,9-dimethyl-phenothiazin-5-ium-3-yl]morpholine, 4-[7-(4,4-difluoro-1-piperidyl)-1,9-dimethylphenothiazin-5-ium-3-yl]morpholine, tert-butyl 4-(1,9-dimethyl-7-morpholino-phenothiazin-5-ium-3-yl)-1,4-diazepane-1-carboxylate, 4-[7-(1,4-diazepan-1-yl)-1,9-dimethyl-phenothiazin-5-ium-3-yl]morpholine, or N-isopropyl-1,9-dimethyl-7-morpholino-phenothiazin-5-ium-3-amine.

22. A compound of claim 1, which is 3-(3-carbamoylpiperidin-1-yl)-1,9-diethyl-7-morpholinophenothiazin-5-ium iodide, 1,9-diethyl-3-morpholino-7-(4-(trifluoromethylsulfonamido)piperidin-1-yl)phenothiazin-5-ium, 1,9-diethyl-3-(4-(1-methylethylsulfonamido)piperidine-1-yl)-7-morpholinophenothiazin-5-ium, 3-(4-cyanopiperidin-1-yl)-1,9-diethyl-7-morpholinophenothiazin-5-ium, 3-(azetidin-1-yl)-1,9-diethyl-7-morpholinophenothiazin-5-ium, 4-(1,9-diethyl-7-morpholino-phenothiazin-5-ium-3-yl)-1,4-thiazine 1,1-dioxide, 3-(4-(cyclopropanesulfonamido)piperidin-1-yl)-1,9-diethyl-7-morpholinophenothiazin-5-ium, or 1,9-diethyl-3-(2-(2-hydroxyethyl)piperidin-1-yl)-7-morpholinophenothiazin-5-ium.

23. A compound of claim 1, which is 1,9-diethyl-3-morpholino-7-(octahydroisoquinolin-2(1H)-yl)phenothiazin-5-ium, or 1,9-diethyl-3-morpholino-7-((4aR,8aS)-octahydroquinolin-1(12H)-yl)phenothiazin-5-ium.

24. A compound of claim 1, which is 1-Ethyl-9-methyl-7-morpholino-3-(thiomorpholin-4,4-dioxide-1-yl)phenothiazin-5-ium, 1-Ethyl-9-methyl-3-morpholino-7-(4-(di-methylamino)piperidin-1-yl)phenothiazin-5-ium, or 1-Ethyl-9-methyl-7-morpholino-3-(4-(N-Boc-amino)piperidin-1-yl)phenothiazin-5-ium.

25. A compound of claim 1, which is 1-ethyl-9-methyl-3-(dimethylamino)-7-(3,5-dimethylmorpholin-1-yl)phenothiazin-5-ium, 1-ethyl-9-methyl-3,7-bis(3,5-dimethyl-morpholin-1-yl)phenothiazin-5-ium, 1-ethyl-9-methyl-3,7-bis(2,6-dimethylmorpholin-1-yl)phenothiazin-5-ium, or 1-ethyl-9-methyl-3-(dimethylamino)-7-(2,6-dimethylmorpholin-1-yl)phenothiazin-5-ium.

26. A compound of claim 1, which is 1-ethyl-9-methyl-7-morpholino-3-(4-aminopiperidin-1-yl)phenothiazin-5-ium.

27. A compound of claim 1, which is 3-(4-(tert-butoxycarbonyl)-1,4-diazepan-1-yl)-1-ethyl-9-methyl-7-morpholino phenothiazin-5-ium.

28. A compound of claim 1, which is 3,7-dimorpholino-1-n-butylphenothiazin-5-ium, 4-(1-tert-butyl-7-morpholino-phenothiazin-5-ium-3-yl)morpholine, 1-sec-butyl-3,7-dimorpholinophenothiazin-5-ium, or 1-isopropyl-3,7-dimorpholino phenothiazin-5-ium.

29. A compound of claim 1, which is 3-(4-(tert-butoxycarbonyl)-1,4-diazepan-1-yl)-1-sec-butyl-7-morpholinophenothiazin-5-ium, 1-sec-butyl-3-(1,4-diazepan-1-yl)-7-morpholinophenothiazin-5-ium, 1-sec-butyl-3-(4-(tert-butylcarbamoyl)-1,4-diazepan-1-yl)-7-morpholinophenothiazin-5-ium, 1-sec-butyl-3-(4-(isopropylsulfonyl)-1,4-diazepan-1-yl)-7-morpholinophenothiazin-5-ium, or 1-sec-butyl-3-(4-(cyclopropylsulfonyl)-1,4-diazepan-1-yl)-7-morpholinophenothiazin-5-ium.

30. A compound of claim 1, which is 3,7-bis-morpholino-1-fluorophenothiazin-5-ium, 3-morpholino-7-(pyrrolidin-1-yl)-1-fluorophenothiazin-5-ium, or 7-(1,4-diazepan-1-yl)-3-morpholino-1-fluorophenothiazin-5-ium.

31. A compound of claim 1, which is 3-dimethylamino-7-morpholino-1-fluorophenothiazin-5-ium or 3-(1,4-diazepan-1-yl)-7-morpholino-1-fluorophenothiazin-5-ium.

32. A compound of claim 1, which is 3,7-bis-morpholino-1,9-difluorophenothiazin-5-ium chloride.

33. A compound of claim 9, wherein said $R^6$ is optionally substituted morpholin-1-yl.

34. A compound of claim 9, having the structure:

wherein each of $R^{30a}$-$R^{33b}$ is selected independently from the group consisting of: hydrogen, halo, cyano, nitro, thio, amino, carboxyl, formyl, and alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cyloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkycarbonyl thi000xy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

35. A compound of claim 34, wherein each of $R^{30a}$-$R^{33b}$ is hydrogen.

36. A compound of claim 34, wherein one of $R^{31a}$ and $R^{31b}$ and one of $R^{32a}$ and $R^{32b}$ is methyl, and $R^{30a}$, $R^{30b}$, $R^{33a}$, and $R^{33b}$ are hydrogen.

37. A compound of claim 34, wherein one of $R^{31a}$ and $R^{31b}$ is carboxyl.

38. A compound of claim 1, wherein $R^6$ is optionally substituted piperazin-1-yl.

39. A compound of claim 6, having the structure:

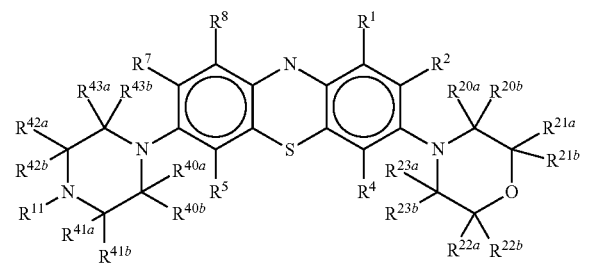

wherein each of $R^{40a}$-$R^{43b}$ is selected independently from the group consisting of: hydrogen, halo, cyano, nitro, thio, amino, carboxyl, formyl, alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkyloxycarbonyloxycarbonyl, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

40. A compound of claim 39, wherein $R^{11}$ and each of $R^{40a}$-$R^{43b}$ is hydrogen.

41. A compound of claim 39, wherein $R^{11}$ is tert-butoxycarbonyl and each of $R^{40a}$-$R^{43b}$ is hydrogen.

42. A compound of claim 39, wherein $R^{11}$ is (tertbutylamino)carbonyl and each of $R^{40a}$-$R^{43b}$ is hydrogen.

43. A compound of claim 1, wherein $R^6$ is optionally substituted piperidin-1-yl.

44. A compound of claim 6, having the structure:

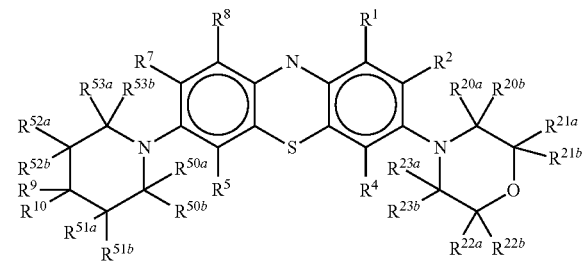

wherein each of $R^{50a}$-$R^{53b}$ is selected independently from the group consisting of: hydrogen, halo, cyano, nitro, thio, amino, carboxyl, formyl, alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkyloxycarbonyloxycarbonyl, carbonylthio, heteroaralkylcarbonyl thio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

45. A compound of claim 44, wherein $R^9$, $R^{10}$ and each of $R^{50a}$-$R^{53b}$ is hydrogen.

46. A compound of claim 44, wherein $R^9$, $R^{10}$ are each fluorine and each of $R^{50a}$-$R^{53b}$ is hydrogen.

47. A compound of claim 44, wherein one of $R^9$ and $R^{10}$ is dimethylamino, and the other and each of $R^{50a}$-$R^{53b}$ is hydrogen.

48. A compound of claim 44, wherein $R^9$ and $R^{10}$ are hydrogen, one of $R^{50a}$ and $R^{53a}$ is aminocarbonyl, and each of the remaining moieties $R^{50a}$-$R^{53b}$ is hydrogen.

49. A compound of claim 1, wherein $R^6$ is optionally substituted piperidin-1-yl.

50. A compound of claim 6, having the structure:

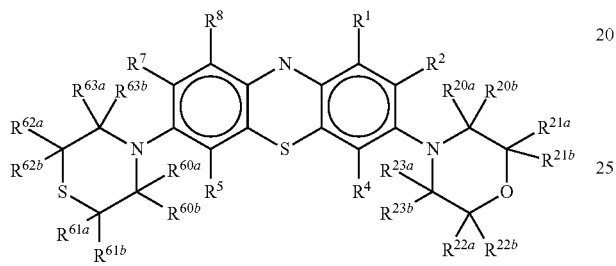

wherein each of $R^{60a}$-$R^{63b}$ is selected independently from the group consisting of: hydrogen, halo, cyano, nitro, thio, amino, carboxyl, formyl, alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkyloxycarbonyloxycarbonyl, carbonylythio, heteroaralkylcarbonyl thio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

51. A compound of claim 1, wherein each of $R^{60a}$-$R^{63b}$ is hydrogen, thus making the ring thiomorpholin-1-yl.

52. A compound of claim 1, wherein $R^6$ is optionally substituted pyrrolidin-1-yl.

53. A compound of claim 6, having the structure:

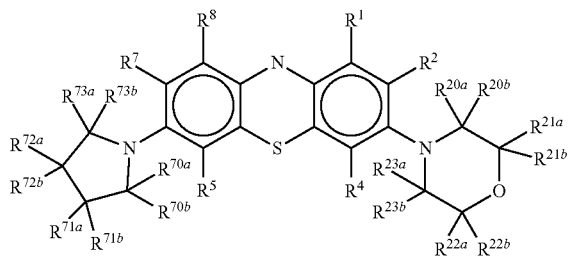

wherein each of $R^{70a}$-$R^{73b}$ is selected independently from the group consisting of: hydrogen, halo, cyano, nitro, thio, amino, carboxyl, formyl, alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkyloxycarbonyloxycarbonyl, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

54. A compound of claim 1, wherein each of $R^{70a}$-$R^{73b}$ drogen.

55. A compound of claim 1, wherein $R^6$ is optionally substituted 1,4-diazepan-1-yl.

56. A compound of claim 6, having the structure:

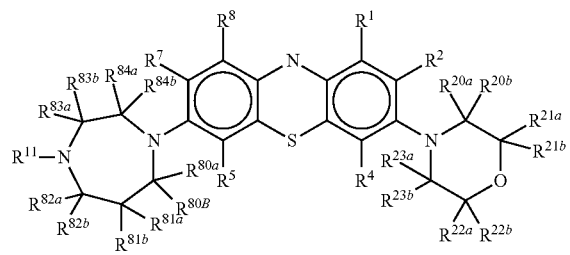

wherein each of $R^{80a}$-$R^{84b}$ is selected independently from the group consisting of: hydrogen, halo, cyano, nitro, thio, amino, carboxyl, formyl, alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkyloxycarbonyloxycarbonyl, carbonylythio, heteroaralkylcarbonylthio, (cycloalkyloxy)carbonylthio, (cycloheteroalkyl)alkylcarbonyl thio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

57. A compound of claim 56, wherein $R^{11}$ and each of $R^{80a}R^{84b}$ is hydrogen.

58. A compound of claim 56, wherein $R^{80a}R^{84b}$ is hydrogen, and $R^{11}$ is boc.

59. A compound of claim 56, wherein $R^{80a}$-$R^{84b}$ is hydrogen, and $R^{11}$ is 2-propylsulfonyl.

60. A compound of claim 1, wherein $R^6$ is optionally substituted azetidin-1-yl.

61. A compound of claim 6, having the structure:

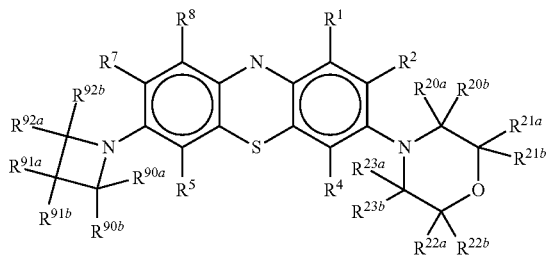

wherein each of $R^{90a}$-$R^{92b}$ is selected independently from the group consisting of: hydrogen, halo, cyano, nitro, thio, amino, carboxyl, formyl, alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkyloxycarbonyloxycarbonyl, carbonylythio, heteroaralkylcarbonylthio, (cycloalkyloxy)carbonylthio, (cycloheteroalkyl)alkylcarbonyl thio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

62. A compound of claim 61, wherein each of $R^{90a}$-$R^{92b}$ is hydrogen.

63. A compound of claim 6, having the structure:

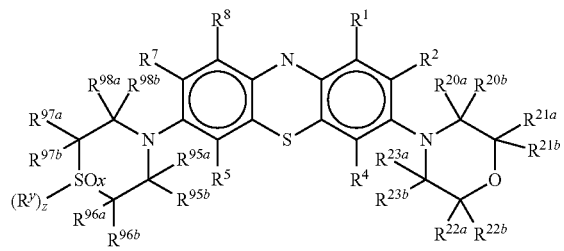

wherein z=0 or 1, and when z=1, then x=1 and y=12, or x=2 and y=13; and each of $R^{95a}$-$R^{98b}$ is selected independently from the group consisting of: hydrogen, halo, cyano, nitro, thio, amino, carboxyl, formyl, and alkyl, alkylcarbonyloxy, aryl carbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkyl carbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkyloxycarbonyloxycarbonyl, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl, each of which is optionally substituted.

64. A compound of claim 1, wherein z=0, y=2, and each of $R^{95a}$-$R^{98b}$ is hydrogen.

\* \* \* \* \*